United States Patent
Chang et al.

(10) Patent No.: US 6,867,866 B1
(45) Date of Patent: Mar. 15, 2005

(54) CD METROLOGY ANALYSIS USING GREEN'S FUNCTION

(75) Inventors: Yia Chung Chang, Champaign, IL (US); Hanyou Chu, San Jose, CA (US); Jon Opsal, Livermore, CA (US)

(73) Assignee: Therma-Wave, Inc., Fremont, CA (US)

( * ) Notice: Subject to any disclaimer, the term of this patent is extended or adjusted under 35 U.S.C. 154(b) by 365 days.

(21) Appl. No.: 10/212,385

(22) Filed: Aug. 5, 2002

Related U.S. Application Data

(60) Provisional application No. 60/394,556, filed on Jul. 9, 2002, provisional application No. 60/378,525, filed on May 7, 2002, and provisional application No. 60/311,427, filed on Aug. 10, 2001.

(51) Int. Cl.$^7$ .............................................. G01B 11/00
(52) U.S. Cl. ...................... 356/446; 356/625; 702/155
(58) Field of Search ............................. 356/600, 601, 356/625, 446; 702/155

(56) References Cited

U.S. PATENT DOCUMENTS

| | | | | |
|---|---|---|---|---|
| 4,548,506 A | * | 10/1985 | Elson | 356/446 |
| 5,880,838 A | * | 3/1999 | Marx et al. | 356/498 |
| 5,963,329 A | | 10/1999 | Conrad et al. | 356/372 |
| 6,429,943 B1 | | 8/2002 | Opsal et al. | 356/625 |
| 6,549,284 B1 | * | 4/2003 | Boas et al. | 356/446 |
| 6,658,144 B1 | * | 12/2003 | Hatab | 382/144 |
| 2002/0035455 A1 | | 3/2002 | Niu et al. | 703/4 |
| 2002/0038196 A1 | | 3/2002 | Johnson et al. | 702/179 |

OTHER PUBLICATIONS

M.G. Moharam et al., "Formulation for stable and efficient implementation of the rigorous coupled–wave analysis of binary gratings," *J. Opt. Soc. Am. A*, vol. 12, No. 5. May 1995, pp. 1068–1076.

R.W. Freund et al., "QMR: a Quasi–Minimal Residual Method for Non–Hermitian Linear Systems," *Num. Math.*, 1991, pp. cover page, 1–33.

L. Li, "New formulation of the Fourier modal method for crossed surface–relief gratings," *J. Opt. Soc. Am A*, vol. 14, No. 10, Oct. 1997, pp. 2758–2767.

P. Paddon et al., "Simple approach to coupling in textured planar waveguides," *Optics Letters*, vol. 23, No. 19, Oct. 1, 1998, pp. 1529–1531.

W. Kong et al., "A Hybrid Analysis of Ellipsometry Data from Patterned Structures," *2000 International Conference on Characterization and Metrology for ULSI Technology* [Final Program and Abstracts, National Institute of Standards and Technology, Gaithersburg, Maryland], Jun. 26–29, 2000, one page in length.

M.E. Lee et al., "Analysis of Reflectometry and Ellipsometry Data from Patterned Structures," *AIP Conference Proc. 449* [University of Michigan], 1998, pp. 1–5.

Oliver J.F. Martin, "Computational eletromagnetics," www.ifh.ee.ethz.ch/~martin/res00.en.html, Jan. 2002, 7 pages in length (printed Nov. 8, 2002).

V. Machavariani et al., "Scatterometry—Interpretation by Different Methods of Electromagnetic Simulation," *Metrology, Inspection, and Process Control for Microlithography XVI, Proceedings of SPIE*, vol. 4689, 2002, pp. 177–188.

* cited by examiner

*Primary Examiner*—Richard A. Rosenberger
(74) *Attorney, Agent, or Firm*—Stallman & Pollock LLP

(57) ABSTRACT

A method for modeling optical scattering includes an initial step of defining a zero-th order structure (an idealized representation) for a subject including a perturbation domain and a background material. A Green's function and a zero-th order wave function are obtained for the zero-th order structure using rigorous coupled wave analysis (RCWA). A Lippmann-Schwinger equation is constructed including the Green's function, zero-th order wave function and a perturbation function. The Lippmann-Schwinger equation is then evaluated over a selected set of mesh points within the perturbation domain. The resulting linear equations are solved to compute one or more reflection coefficients for the subject.

35 Claims, 2 Drawing Sheets

CD METROLOGY ANALYSIS USING GREEN'S FUNCTION

The present application claims priority to U.S. Provisional Patent Applications Ser. No. 60/311,427, filed Aug. 10, 2001, Ser. No. 60/378,525, filed May 7, 2002 and Ser. No. 60/394,556, filed Jul. 9, 2002 all of which are incorporated herein by reference.

TECHNICAL FIELD

The subject invention relates to a technique for determining the scattering response of a periodic structure using a Green's function approach in combination with rigorous coupled wave analysis.

BACKGROUND OF THE INVENTION

Over the past several years, there has been considerable interest in using optical scatterometry (i.e., optical diffraction) to perform critical dimension (CD) measurements of the lines and structures included in integrated circuits. Optical scatterometry has been used to analyze periodic two-dimensional structures (e.g., line gratings) as well as three-dimensional structures (e.g., patterns of vias or mesas). Scatterometry is also used to perform overlay registration measurements. Overlay measurements attempt to measure the degree of alignment between successive lithographic mask layers.

Various optical techniques have been used to perform optical scatterometry. These techniques include broadband scatterometry (U.S. Pat. Nos. 5,607,800; 5,867,276 and 5,963,329), spectral ellipsometry (U.S. Pat. No. 5,739,909) as well as spectral and single-wavelength beam profile reflectance (BPR) and beam profile ellipsometry (BPE) (U.S. Pat. No. 6,429,943). In addition it may be possible to employ single-wavelength laser BPR or BPE to obtain CD measurements on isolated lines or isolated vias and mesas.

Most scatterometry systems use a modeling approach to transform scatterometry signals into critical dimension measurements. For this type of approach, a theoretical model is defined for each physical structure that will be analyzed. The theoretical model predicts the empirical measurements (scatterometry signals) that scatterometry systems would record for the structure. A rigorous coupled wave theory can be used for this calculation. The theoretical results of this calculation are then compared to the measured data (actually, the normalized data). To the extent the results do not match, the theoretical model is modified and the theoretical data is calculated once again and compared to the empirical measurements. This process is repeated iteratively until the correspondence between the calculated theoretical data and the empirical measurements reaches an acceptable level of fitness. At this point, the characteristics of the theoretical model and the physical structure should be very similar.

The calculations discussed above are relatively complex even for simple models. As the models become more complex (particularly as the profiles of the walls of the features become more complex) the calculations become exceedingly long and complex. Even with high-speed processors, real time evaluation of these calculations can be difficult. Analysis on a real time basis is very desirable so that manufacturers can immediately determine when a process is not operating correctly. The need is becoming more acute as the industry moves towards integrated metrology solutions wherein the metrology hardware is integrated directly with the process hardware.

A number of approaches have been developed to overcome the calculation bottleneck associated with the analysis of scatterometry results. Many of these approaches have involved techniques for improving calculation throughput, such as parallel processing techniques. An approach of this type is described in a co-pending application Ser. No. 09/818,703 filed Mar. 27, 2001 which describes distribution of scatterometry calculations among a group of parallel processors. In the preferred embodiment, the processor configuration includes a master processor and a plurality of slave processors. The master processor handles the control and the comparison functions. The calculation of the response of the theoretical sample to the interaction with the optical probe radiation is distributed by the master processor to itself and the slave processors.

For example, where the data is taken as a function of wavelength, the calculations are distributed as a function of wavelength. Thus, a first slave processor will use Maxwell's equations to determine the expected intensity of light at selected wavelengths scattered from a given theoretical model. The other slave processors will carry out the same calculations at different wavelengths. Assuming there are five processors (one master and four slaves) and fifty wavelengths, each processor will perform ten such calculations per iteration.

Once the calculations are complete, the master processor performs the best fit comparison between each of the calculated intensities and the measured normalized intensities. Based on this fit, the master processor will modify the parameters of the model as discussed above (changing the widths or layer thickness). The master processor will then distribute the calculations for the modified model to the slave processors. This sequence is repeated until a good fit is achieved.

This distributed processing approach can also be used with multiple angle of incidence information. In this situation, the calculations at each of the different angles of incidence can be distributed to the slave processor. Techniques of this type are an effective method for reducing the time required for scatterometry calculations. At the same time, the speedup provided by parallel processing is strictly dependent on the availability (and associated cost) of multiple processors. Amdahl's law also limits the amount of speedup available by parallel processing since serial portions program portions are not improved. At the present time, neither cost nor ultimate speed improvement is a serious limitation for parallel processing techniques. As geometries continue to shrink, however it becomes increasingly possible that computational complexity will outstrip the use of parallel techniques alone.

Another approach is to use pre-computed libraries of predicted measurements. This type of approach is discussed in PCT application WO 99/45340, published Sep. 10, 1999 as well as the references cited therein. In this approach, the theoretical model is parameterized to allow the characteristics of the physical structure to be varied. The parameters are varied over a predetermined range and the theoretical result for each variation to the physical structure is calculated to define a library of solutions. When the empirical measurements are obtained, the library is searched to find the best fit.

The use of libraries speeds the analysis process by allowing theoretical results to be computed once and reused many times. At the same time, library use does not completely solve the calculation bottleneck. Construction of libraries is time consuming, requiring repeated evaluation of the same time consuming theoretical models. Process changes and other variables may require periodic library modification or replacement at the cost of still more calculations. For these reasons, libraries are expensive (in computational terms) to build and to maintain. Libraries are also necessarily limited in their resolution and can contain only a finite number of theoretical results. As a result, there are many cases where empirical measurements do not have exact library matches. One approach for dealing with this problem is to generate additional theoretical results in real time to augment the theoretical results already present in the library. This combined approach improves accuracy, but slows the scatterometry process as theoretical models are evaluated in real time. A similar approach is to use a library as a starting point and apply an interpolation approach to generate missing results. This approach avoids the penalty associated with generating results in real time, but sacrifices accuracy during the interpolation process.

For these reasons and others, there is a continuing need for faster methods for computing theoretical results for scatterometry systems. This is true both for systems that use real time evaluation of theoretical models as well as systems that use library based problem solving. The need for faster evaluation methods will almost certainly increase as models become more detailed to more accurately reflect physical structures.

SUMMARY OF THE INVENTION

The present invention provides a method for modeling optical diffraction. The modeling method is intended to be used in combination with a wide range of subjects including semi-conductor wafers and thin films. A generic subject includes a scatterer sandwiched between a foreground material and a background material. The scatterer is a periodic or isolated structure and may be two or three-dimensional. The background material includes each of the layers of the subject that are situated below the scatterer. The foreground material includes all of the substances (in some cases this includes layers of the subject) that overlay the scatterer.

The modeling method begins with the construction of an idealized representation (also known as the zero-th order structure) for the subject being modeled. The idealized representation is based on one of three templates. The templates are referred to as the G0, G1 and Ga structures, respectively. Each of these templates is a combination of the subject's background material and a perturbation domain. The perturbation domain contains the scatterer and is treated differently by each template. The perturbation domain in the G0 structure has a dielectric response that is equivalent to the subject's foreground. For the G1 structure, the perturbation domain includes a grating. The grating consists of a limited number of square slabs arranged in a repeating pattern closely modeling the scatterer. For the Ga case, the perturbation domain contains a uniform medium. A wide range of functions may be used to define the dielectric properties of the uniform medium. For one such function, the TE mode response is defined to be a weighted average of the dielectric function for the scatterer and the foreground material. The TM mode response is similar except that the inverse of the dielectric function is used to compute the weighted average.

One or more Lippmann-Schwinger wave equations are used to represent the idealized representation. Each wave equation includes a wave function for the zero-th order structure, a Green's function for the zero-th order structure and a perturbation function. The wave function for the zero-th order structure and the Green's function arm obtained using rigorous coupled wave analysis. The perturbation function describes the dielectric properties of the perturbation domain. By definition, the perturbation function is defined to be zero at all points outside of the perturbation domain. As a result, numerical evaluation of the Lippmann-Schwinger wave equations may be limited to the area within the perturbation domain, greatly accelerating numerical evaluation of the scattering response.

The perturbation domain is subdivided into a series of segments or layers. The Lippmann-Schwinger wave equations are then evaluated in each segment. The result of this repeated evaluation is a system of linear equations. Each equation within the system relates the terms of the wave equations obtained in a particular segment of the perturbation domain for a particular coupled wave.

The system of linear equations is solved to obtain one or more reflection coefficients for the idealized representation. This can be done using any iterative solver. Typical solvers include the quasi-minimal-residue (QMR), TMRES and Krylov subspace solvers. Other suitable techniques may also be used.

In this way, an efficient method for modeling optical diffraction is provided. The efficiency of this method is enhanced because the numerical evaluation is limited to the perturbation domain of the idealized representation. Efficiency is further enhanced because the boundaries between the perturbation domain and the remaining layers of the zero-th order structure are intrinsically accounted for by the Green's function.

DETAILED DESCRIPTION OF THE PREFERRED EMBODIMENTS

Overview

Figure 1:
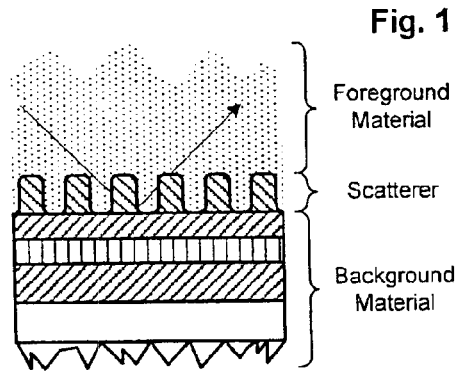
FIG. 1 shows a cross sectional representation of a generic subject for which optical diffraction may be modeled.

The present invention provides a method for modeling optical diffraction. The modeling method is intended to be used in combination with a wide range of subjects including semi-conductor wafers and thin films. As shown in FIG. 1, the cross section for a generic subject reveals a scatterer sandwiched between a foreground material and a background material. The scatterer is a periodic or isolated structure and may be two or three-dimensional. For semi-conductor wafers, single lines are typical examples of two-dimensional isolated scatterers. Parallel groups of lines evenly spaced are a common example of two-dimensional periodic scatterers. Single vias are an example of isolated three-dimensional scatterers. In groups, vias can be an example of periodic three-dimensional scatterer.

The background material includes each of the layers situated below the scatterer. For the case of semi-conductor wafers, the background material would typically be a multilayer dielectric film. The foreground material includes all of the substances that overlay the scatterer. Where the scatterer forms the surface of the subject, the foreground material includes the overlaying gas, fluid or vacuum. In cases where the scatterer is submerged within the subject, the foreground material includes the overlaying layers.

Figure 2:
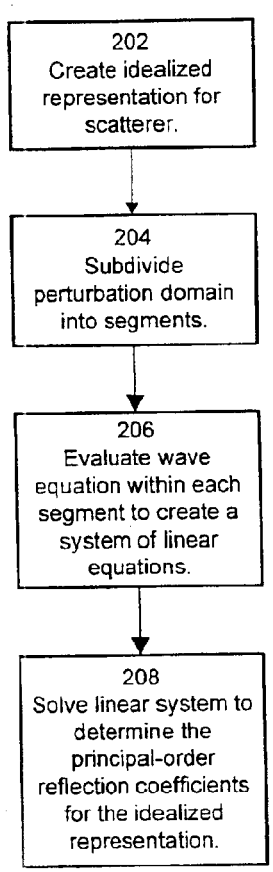
FIG. 2 is a flowchart showing the steps associated with a method for modeling optical scattering as provided by an embodiment of the present invention.

The modeling method begins with a subject (such as the subject of FIG. 1) and computes one or more reflection coefficients. A high level flowchart showing the steps associated with this method is shown in FIG. 2. As may be seen in step 202 of that figure, the modeling method begins with the construction of an idealized representation (also known as the zero-th order structure) for the subject being modeled.

Figure 3:
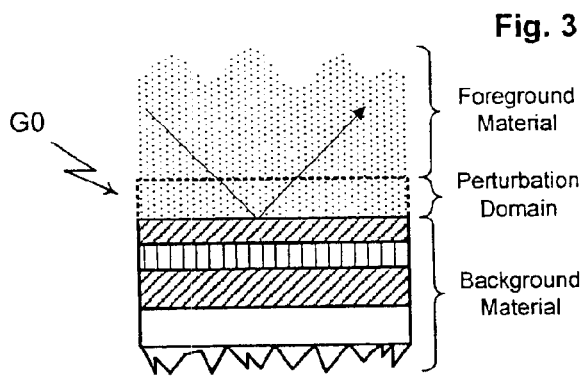
FIG. 3 is a cross sectional representation of the G0 structure as used by an embodiment of the present invention.

The idealized representation is based on one of three templates. The templates are referred to as the G0, G1 and Ga structures, respectively. As shown in FIG. 3, the G0 structure retains the background material described for the generic subject shown in FIG. 1. The scatterer is replaced by a uniform medium that has a dielectric response that is equivalent to the subject's foreground.

Figure 4:
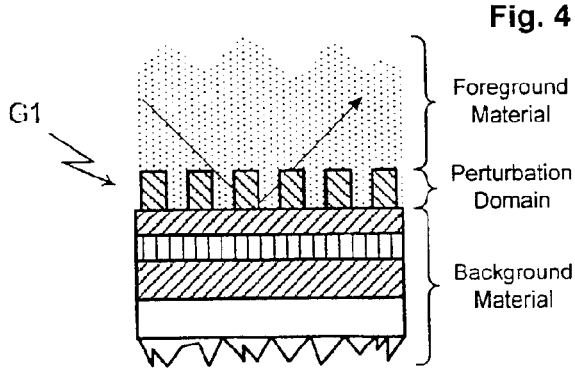
FIG. 4 is a cross sectional representation of the G1 structure as used by an embodiment of the present invention.

The G1 structure (shown in FIG. 4) includes the same background material described for the G0 structure. Unlike the G0 structure, the perturbation domain of the G1 structure includes a grating. The grating consists of a limited number of square slabs arranged in a repeating pattern. The square slabs closely model the scatterer.

The Ga structure (not shown) shares the background material of the G0 and G1 structures. The perturbation domain of the Ga case contains a uniform medium. A wide range of functions may be used to define the dielectric properties of the uniform medium. For one such function, the TE mode response is defined to be a weighted average of the dielectric function for the scatterer and the foreground material. The TM mode response is similar except that the inverse of the dielectric function is used to compute the weighted average.

The G0, G1, and Ga structures offer various tradeoffs for computational speed and accuracy. The G1 structure is generally the most computationally intensive. The G0 is generally the least computationally intensive. Selection of a particular structure is also dependent on the type of subject. The G1 structure works best when used for two-dimensional analysis. This type of analysis is appropriate for subjects that include two-dimensional scatterers (scatterers that exhibit a translational symmetry along an axis). The G0 and Ga structures, on the other hand, may be used for both two and three dimensional analysis. In step 202, one of the three structures is selected and used to create the idealized representation for the subject.

The remaining steps of the modeling method are devoted to numerical evaluation of the scattering response of the idealized representation. To avoid confusion, it should be noted that several derivations have been developed to perform this evaluation. This overview section briefly describes one of these derivations with additional description for all derivations provided in subsequent portions of this document. For each derivation, the numerical evaluation is based on the use of one or more Lippmann-Schwinger equations to represent one or more wave functions for the idealized representation. In the coupled wave basis, each of these equations has a form similar to (and for some derivations identical to):

$$\Psi(z) - \Psi_0(z) = \int dz' G(z, z') V(z') \Psi(z'). \quad (1.1)$$

Within Equation (1.1) $\Psi_0(z)$ and $G(z, z')$ are the wave and Green's functions for the zero-th order structure. $V(z')$ is known as the perturbation function and describes the dielectric properties of the perturbation domain. By definition, the perturbation function is defined to be zero at all points outside of the perturbation domain. As a result, numerical evaluation of Equation (1.1) may be limited to the area within the perturbation domain, greatly accelerating numerical evaluation of the scattering response.

Figure 5:
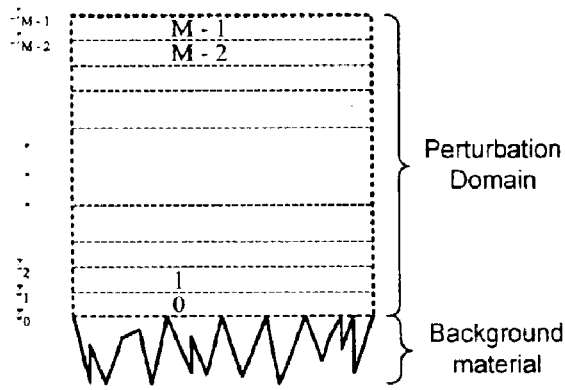
FIG. 5 is a cross sectional representation of the perturbation domain of the G0 structure after subdivision.

To evaluate Equation (1.1), the modeling method subdivides the perturbation domain into a series of segments, each having the same thickness (see step 204). This type of subdivision for a G0-type perturbation domain is shown in FIG. 5.

Equation (1.1) is then evaluated in each segment (see step 206). The result of this repeated evaluation is a system of linear equations. Each equation within the system relates the terms of Equation (1.1) obtained in a particular segment of the perturbation domain for a particular coupled wave.

The system of linear equations is then solved to obtain one or more reflection coefficients for the idealized representation (see step 208). This can be done using any iterative solver. Typical solvers include the quasi-minimal-residue (QMR), TMRES and Krylov subspace solvers. Other suitable techniques may also be used.

The modeling method of FIG. 2 provides an efficient method for modeling optical diffraction. The efficiency of this method is enhanced because the numerical evaluation is limited to the perturbation domain of the idealized representation. Efficiency is further enhanced because the boundaries between the perturbation domain and the remaining layers of the zero-th order structure are intrinsically accounted for by the Green's function. As described above, the modeling method is suitable for the analysis of TE modes for two-dimensional structures (i.e., structures that exhibit a translational symmetry in one direction). The following sections describe derivations for two and three dimensional structures for TE and TM modes.

Equation Section 2Wave Equations for Two-dimensional Structures

This section describes derivations for separate TE and TM mode wave equations for two-dimensional structures. The wave equations allow the modeling method to be used to predict the diffraction response of two-dimensional structures (i.e., structures that exhibit translational symmetry in at least one direction). For semi-conductor wafers, this can include patterns of lines and other periodic structures.

For TE modes the wave function $\psi(x, z)$ of concern is the y-component of the electric field ($E_y$). From Maxwell's equations, $E_y$ satisfies the following differential equation:

$$[\partial_x^2 + \partial_z^2 + k_0^2 \in(x, z)]\psi(x, z) = 0, \quad (2.1)$$

where $\in(x, z)$ is the position-dependent dielectric function, $k_0 = 2\pi/\lambda_0$, and $\lambda_0$ is the wavelength of the incident radiation in free space. Equation (2.1) is subject to the boundary conditions that $\psi$ and $\partial_z \psi$ are continuous. Replacing $\in(x, z)$ with $\in_0(x, z)$ yields a similar equation for the zero-th order structure:

$$[\partial_x^2 + \partial_z^2 + k_0^2 \in_0(x, z)]\psi_0(x, z) = 0,$$

A corresponding Green's function $G(x, z; x, z')$ may be formulated as:

$$[\partial_x^2 + \partial_z^2 + k_0^2 \in_0(x, z)]G(x, z; x', z') = \delta(z-z')\delta(x-x') \quad (2.2)$$

subject to the same boundary conditions that $\psi$ and $\partial_z \psi_0$ are continuous.

To determine the scattering response of the idealized representation, it is necessary to account for the dielectric properties of the perturbation domain. This perturbation is denoted V. Within the perturbation domain (0<z<d) $V(x, z)=[\in(x, z)-\in_0]k_0^2$. At all other points, V is zero.

The perturbation function V, the Green's function G(x, z; x, z'), and the wave function for the zero-th order structure $\psi_0$ are used to obtain a wave function $\psi$ for the idealized representation. $\psi$ is a Lippmann-Schwinger equation having the following form:

$$\psi(x, z) - \psi_0(x, z) = \int dx'dz' G(x, z; x', z') V(x', z') \psi(x', z'). \quad (2.3)$$

Projecting equation (2.3) into the coupled wave basis with $<x|n>=e^{ik_0 x}/\sqrt{p}(k_n=k_{0x}+2\pi n/p)$, yields:

$$\Psi(z) - \Psi_0(z) = \int dz' G(z, z') V(z') \Psi(z'), \quad (2.4)$$

where $\Psi$ and $\Psi_0$ are N dimensional column vectors with entries given by: $\Psi_n(z)=<n|\psi>$ and $\Psi_n^0(z)=<n|\psi_0>$. G and V are N×N matrices with elements given by $G_{n,n'}(z, z')=<n|G|n'>$ and $V_{n,n'}(z)=<n|V|n'>$.

For TM modes the wave function $\psi(x, z)$ of concern is the y-component of the magnetic field ($H_y$). From Maxwell's equations, ($H_y$) satisfies the following differential equation:

$$[\partial_x \in^{-1} \partial_x + \partial_z \in^{-1} \partial_z + k_0^2] \psi(x, z) = 0 \quad (2.5)$$

subject to the boundary conditions that $\psi(x, z)$ and $\in^{-1} \partial_z \psi(x, z)$ are continuous across a z boundary and $\psi(x, z)$ and $\in^{-1} \partial_x \psi(x, z)$ are continuous across a x boundary. Note that the discontinuity of $\partial_x H_y$ across x boundaries causes slow convergence in the coupled-wave method. So, more plane waves are needed for the expansion of $H_y$ field than for the $E_y$ field. Replacing $\in(x, z)$ with $\in_0(x, z)$ yields a similar differential equation for the unperturbed system (zero-th order structure):

$$[\partial_x \in_0^{-1} \partial_x + \partial_z \in_0^{-1} \partial_z + k_0^2] \psi_0(x, z) = 0 \quad (2.6)$$

A corresponding Green's function G(x, z; x, z') may be formulated as:

$$[\partial_x \in_0^{-1} \partial_x + \partial_z \in_0^{-1} \partial_z + k_0^2] G^0(x, z; x', z') = \delta(x-x') \delta(z-z') \quad (2.7)$$

subject to the same set of boundary conditions required for $\psi_0(x, z)$.

To construct a wave equation for TM modes, Equation (2.7) is multiplied by $\psi(x', z') - \psi_0(x', z')$ and integrated over x' and z'. Equation (2.6) is multiplied by G(x, z; x', z') and integrating over x' and z'. The difference of the two resulting equations yields a Lippmann-Schwinger equation for the TM modes having the following form:

$$\psi(x, z) - \psi_0(x, z) = \quad (2.8)$$

$$\int dx'dz' [\partial_{x'} G(x, z;, x', z')] V(x', z') [\partial_{x'} \psi(x, z;, x', z')] +$$

$$\int dx'dz' [\partial_{z'} G(x, z;, x', z')] V(x', z') [\partial_{z'} \psi(x', z')],$$

where $V(x, z)=\in^{-1}(x, z) - \in_0^{-1}(x, z)$ is the perturbation in inverse dielectric function. To derive Equation (2.8), integration by parts is used. The boundary terms generated in the process vanish exactly due to the fact that the derivatives of $\psi$ (or G) divided by $\in$ (or $\in_0$) are continuous across the corresponding boundaries.

Projecting the above equations into the coupled wave basis yields:

$$\Psi(z) - \Psi^0(z) = \int dz [G(z, z') K \tilde{V}(z') K \Psi(z') + \partial_z G(z, z') V(z') \partial_z \Psi(z')]. \quad (2.9)$$

where K is a diagonal matrix with the n-th diagonal entry given by $k_n$.

For TM modes, two types of perturbation matrices are used: V and $\tilde{V}$. The first type is defined as $V=P-P_0$, where $P(P_0)$ is a matrix of the inverse dielectric function with elements given by $P_{n,n'}(z)=<n|1/\in|n'>$. The second type is defined as: $\tilde{V}=E^{-1}-E_0^{-1}$, where $E^{-1}$ is the inverse of dielectric function matrix (E), whose matrix elements are $E_{n,n'}(z)=<n|\in|n'>$ and similarly for $E_0$. V and $\tilde{V}$ are identical when a complete set of coupled-wave basis functions is used. In practice, a finite number of coupled-wave basis functions are used, and to achieve fast convergence, $\tilde{V}$ is used for terms involving x-derivatives and V for terms involving z-derivatives. The use of V and $\tilde{V}$ perturbation matrices takes advantage of the observation that calculation of a Fourier transform involving a continuous function $[1/\in(x)]$ $[\partial_x \psi(x)]$ which is the product of two discontinuous functions $[1/\in(x)]$ and $[\partial_x \psi(x)]$ converges more rapidly if the resulting product matrix is expressed as $[\in]^{-1}[\psi]$ rather than $[1/\in]$ $[\psi]$. This observation is discussed in (L. Li, J. Opt. Soc. Am. A 2758 (1997)). That article is incorporated in this document by reference.

Efficient Transfer-matrix Method for RCWA

In order to optimize the efficiency of the algorithm, an efficient transfer-matrix method is used to calculate the matrices and wave functions needed for constructing the Green's function within the coupled-wave basis. The derivation for this method takes advantage of the symmetry properties of the matrices whenever possible, thus making the coding more efficient.

For both TE and TM modes, the differential equations projected within the coupled-wave basis (i.e., equations (2.4) and (2.9)) can be cast into the general form:

$$\left(\frac{d}{dz} D(z) \frac{d}{dz} + H(z)\right) \Psi(z) = 0. \quad (2.10)$$

D and H are square matrices of dimension N and $\Psi$ is a vector of dimension N (the number of coupled waves used). For TE modes, D=1 and $H(z)=E(z)k_0^2-K^2$, where E(z) is the dielectric matrix. For TM modes, D=P(z) (P is the matrix of inverse dielectric function) and $H(z)=k_0^2-KE^{-1}(z)K$, where K is a diagonal matrix with elements $k_n=k_{0x}+2\pi n/p$. Both D(z) and H(z) are piecewise-constant functions of z.

The general solution to the wave function $\Psi(z)$ in each layer of the structure where D and H are independent of z can be expressed as:

$$\Psi = \sum_n s_n e^{-q_n z} f_n + \sum_n s_n e^{q_n z} g_n \equiv Se^{-Qz} f + Se^{Qz} g, \quad (2.11)$$

$$\partial \Psi \propto \sum_n s_n(-q_n) e^{-q_n z} f_n + \sum_n s_n q_n e^{q_n z} g_n \equiv SQe^{-Qz} f + SQe^{Qz} g, \quad (2.12)$$

where f and g are the vectors formed by $f_n$'s and $g_n$'s which are to be determined by the boundary conditions. Q is a diagonal matrix formed by the exponents $q_n$. The wave functions are arranged in such a way that $e^{-q_n z}$ represents the decaying (evanescent) wave in the positive z-direction when the real part of $q_n$ is non-zero, and it is the physical forward propagating wave when $q_n$ is imaginary. $e^{q_n z}$ represents the growing wave and is therefore not allowed in the substrate region. The S matrix consists of the eigenvectors of Equation (2.10), and satisfies:

$$HS=\lambda DS,$$

which can be solved via a standard LAPACK routine. The exponents are related to the eigenvalues of H via $\sqrt{-\lambda_n}=q_n^2$ with non-negative real parts. Note that both H and D are symmetric matrices. As a result, the relation $S^{-1}=S^T D$ applies, where $S^T$ is the transpose of S. This relation will be used to evaluate $S^{-1}$ directly without performing the time-consuming matrix inversion.

The boundary conditions are determined by requiring that the wave function $\Psi(z)$ and the generalized current be continuous across material boundaries. In the present case, the current is proportional to $D(z)\partial_z \Psi(z)$ yielding:

$$\begin{pmatrix} \Psi \\ D\partial_z \Psi \end{pmatrix} = \begin{pmatrix} S & S \\ -DSQ & -DSQ \end{pmatrix}\begin{pmatrix} e^{-Qz} & 0 \\ 0 & e^{Qz} \end{pmatrix}\begin{pmatrix} f \\ g \end{pmatrix} \quad (2.13)$$

$$= \begin{pmatrix} S & 0 \\ 0 & -DSQ \end{pmatrix}\begin{pmatrix} 1 & 1 \\ 1 & -1 \end{pmatrix}\begin{pmatrix} e^{-Qz} & 0 \\ 0 & e^{Qz} \end{pmatrix}\begin{pmatrix} f \\ g \end{pmatrix} \quad (2.14)$$

$$\equiv \begin{pmatrix} S & 0 \\ 0 & J \end{pmatrix}\tau \begin{pmatrix} e^{-Qz} & 0 \\ 0 & e^{Qz} \end{pmatrix}\begin{pmatrix} f \\ g \end{pmatrix}. \quad (2.15)$$

where J stands for generalized current matrix. Note that all the elements are themselves matrices. The matrix $\tau$ has the property that:

$$\tau^{-1} = \frac{1}{2}\tau.$$

Throughout this description, z in the wave functions for each layer l is measured relative to the interface between layers l–1 and l. The boundary conditions are usually in the following form:

$$\begin{pmatrix} S_l & 0 \\ 0 & J_l \end{pmatrix}\tau\begin{pmatrix} e^{-Q_l d_l} & 0 \\ 0 & e^{Q_l d_l} \end{pmatrix}\begin{pmatrix} f_l \\ g_l \end{pmatrix} = \begin{pmatrix} S_{l+1} & 0 \\ 0 & J_{l+1} \end{pmatrix}\tau\begin{pmatrix} f_{l+1} \\ g_{l+1} \end{pmatrix} \quad (2.16)$$

Denoting:

$$M_l = S_l^{-1} S_{l+1}, N_l = J_l^{-1} J_{l+1} \quad (2.17)$$

produces the relation:

$$\begin{pmatrix} f_l \\ g_l \end{pmatrix} = \frac{1}{2}\begin{pmatrix} e^{Q_l d_l} & 0 \\ 0 & e^{-Q_l d_l} \end{pmatrix}\begin{pmatrix} 1 & 1 \\ 1 & -1 \end{pmatrix}\begin{pmatrix} M_l & 0 \\ 0 & N_l \end{pmatrix}\begin{pmatrix} 1 & 1 \\ 1 & -1 \end{pmatrix}\begin{pmatrix} f_{l+1} \\ g_{l+1} \end{pmatrix} \quad (2.18)$$

$$= \frac{1}{2}\begin{pmatrix} e^{Q_l d_l} & 0 \\ 0 & e^{-Q_l d_l} \end{pmatrix}\begin{pmatrix} M_l + N_l & M_l - N_l \\ M_l - N_l & M_l + N_l \end{pmatrix}\begin{pmatrix} f_{l+1} \\ g_{l+1} \end{pmatrix} \quad (2.19)$$

$$= \begin{pmatrix} e^{Q_l d_l} & 0 \\ 0 & e^{-Q_l d_l} \end{pmatrix}\begin{pmatrix} M_l^+ & M_l^- \\ M_l^- & M_l^+ \end{pmatrix}\begin{pmatrix} f_{l+1} \\ g_{l+1} \end{pmatrix} \equiv \begin{pmatrix} f_{l+1} \\ g_{l+1} \end{pmatrix} \quad (2.20)$$

This is the starting point of the transfer matrix approach. Let t be the transmission coefficient at the substrate layer (labeled by L), this yields:

$$\begin{pmatrix} f_l \\ g_l \end{pmatrix} = \prod_{l=j}^{L-1} \tau_l \begin{pmatrix} t \\ 0 \end{pmatrix} = T_l \begin{pmatrix} t \\ 0 \end{pmatrix} = \begin{pmatrix} \tau_{11} & \tau_{12} \\ \tau_{21} & \tau_{22} \end{pmatrix}\begin{pmatrix} t \\ 0 \end{pmatrix} = \begin{pmatrix} \tau_{11} t \\ \tau_{21} t \end{pmatrix}$$

It is important to note that only the first column of the matrix $T_l$ is needed. This fact reduces transfer matrix computational time.

The transfer matrix formalism can be unstable due to exponentially growing factors $e^{Q_l d_l}$, even in the spirit of the above format (although a simple scaling can be applied in the single component case). It turns out that it is possible to overcome this difficulty, provided that the growing and decaying waves are cleanly separated. To achieve this goal, the following equation is used:

$$\begin{pmatrix} f_l \\ g_l \end{pmatrix} = \begin{pmatrix} f_l \\ R_l f_l \end{pmatrix} \quad (2.21)$$

Equation (2.20) gives:

$$f_l = e^{Q_l d_l}(M_l^+ + M_l^- R_{l+1}) f_{l+1} \quad (2.22)$$

$$R_l f_l = e^{Q_l d_l}(M_l^- + M_l^+ R_{l+1}) f_{l+1} \quad (2.23)$$

These equations may be rewritten as:

$$f_{l+1} = (M_l^+ + M_l^- R_{l+1})^{-1} e^{-Q_l d_l} f_l \equiv T_l e^{-Q_l d_l} f_l \quad (2.24)$$

$$R_l = e^{-Q_l d_l}(M_l^- + M_l^+ R_{l+1})(M_l^+ + M_l^- R_{l+1})^{-1} e^{-Q_l d_l} \quad (2.25)$$
$$= e^{-Q_l d_l}(M_l^- + M_l^+ R_{l+1}) T_l e^{-Q_l d_l}$$

Using $R_l = e^{-Q_l d_l}\bar{R}_l e^{-Q_l d_l}$, gives:

$$\bar{R}_l = (M_l^- + M_l^+ e^{-Q_{l+1} d_{l+1}} \bar{R}_{l+1} e^{-Q_{l+1} d_{l+1}}) T_l. \quad (2.26)$$

Equation (2.25) is obtained by replacing $f_{l+1}$ within Equation (2.23) with the derivation for $f_{l+1}$ obtained in Equation (2.24) and then equating the coefficient of $f_l$. The recursion process is stable. If the wave function is not required, Equation (2.24) is not needed. In that case, Equation (2.25) is solved by starting with the base case $R_L = 0$ (in the substrate layer). If the wave function is required, $T_l$ is calculated using Equation (2.24). Equation (2.24) is then used to recursively obtain $f_l$, with $f_0$ the incident wave function which is known, then $g_l = R_l f_l$. The growing wave is also well controlled since $R_l = e^{-Q_l d_l}\bar{R}_l e^{-Q_l d_l}$, where $\bar{R}_l$ is finite, and $e^{Q_l z} R_l f_l = e^{-Q_l(d_l - z)} \bar{R}_l e^{-Q_l d_l} f_l$ is well defined.

For calculating the Green's function (which will be discussed below), it is necessary to obtain a transfer matrix calculation that starts from the incident medium. For this derivation, define $m_l = M_l^{-1} = S_{l+1}^{-1} S_l = Q_{l+1}^{-1} N_l^T Q_l$ and $n_l = N_l^{-1} = J_{l+1}^{-1} J_l = Q_{l+1} M_l^T Q_l^{-1}$. Note that the calculation of $m_l$ and $n_l$ only involves a matrix transposition. Equation (2.19) becomes:

$$\begin{pmatrix} f_{l+1} \\ g_{l+1} \end{pmatrix} = \frac{1}{2}\begin{pmatrix} m_l + n_l & m_l - n_l \\ m_l - n_l & m_l + n_l \end{pmatrix}\begin{pmatrix} e^{-Q_l d_l} & 0 \\ 0 & e^{Q_l d_l} \end{pmatrix}\begin{pmatrix} f_l \\ g_l \end{pmatrix} \quad (2.27)$$

Similar to the forward cases, define $f_l = \bar{r}_l g_l$, and the above equation becomes:

$$\begin{pmatrix} r_{l+1} g_{l+1} \\ g_{l+1} \end{pmatrix} = \frac{1}{2}\begin{pmatrix} m_l + n_l & m_l - n_l \\ m_l - n_l & m_l + n_l \end{pmatrix}\begin{pmatrix} e^{-Q_l d_l} & 0 \\ 0 & e^{Q_l d_l} \end{pmatrix}\begin{pmatrix} r_l g_l \\ g_l \end{pmatrix} \quad (2.28)$$

which can be rewritten as:

$$g_{l+1} = (m^+ + m^- e^{-Q_l d_l} \bar{r}_l e^{-Q_l d_l}) e^{Q_l d_l} g_l \quad (2.29)$$

$$\bar{r}_{l+1} g_{l+1} = (m^- + m^+ e^{-Q_l d_l} \bar{r}_l e^{-Q_l d_l}) e^{Q_l d_l} g_l$$

$$g_l = e^{-Q_l d_l} (m^+ + m^- e^{-Q_l d_l} \bar{r}_l e^{-Q_l d_l})^{-1} g_{l+1}$$

$$\equiv e^{Q_l d_l} t_l g_{l+1}$$

$$\bar{r}_{l+1} = (m^- + m^+ e^{-Q_l d_l} \bar{r}_l e^{-Q_l d_l})(m^+ + m^- e^{Q_l d_l} \bar{r}_l e^{-Q_l d_l})^{-1} \quad (2.30)$$

$$\equiv (m^- + m^+ e^{-Q_l d_l} \bar{r}_l e^{-Q_l d_l}) t_l$$

Note that the backward and forward transfer matrix formalisms are the same, (compare this equation with Equation (2.26)). The difference only lies in the reference point for z.

Green's Function within the Coupled-wave Basis

To calculate Green's functions for a multi-component layered system, it is best to use a source term that is more convenient than the wave function expansion. In this way, the Green's function is calculated in the same way as the wave function except for the complication originated from the source term. Within the coupled-wave basis:

$$\left(\frac{d}{dz} D(z) \frac{d}{dz} + H(z)\right) G(z, z') = \delta(z - z'). \quad (2.31)$$

Since there is no incident wave, the wave propagates from the source in both directions. Thus, in either the substrate or incident medium there are only decaying waves. The coefficients of the decaying waves must be zero. Using the notations defined for the wave functions, the coefficients g in the substrate and f in the incident medium must be zero, which are the governing boundary conditions for Green's function calculations.

If the source is located inside layer 1 and G(z, z') is continuous across the plane z=z', then integrating the equation of motion over z near the boundary plane yields:

$$\begin{pmatrix} G(z'^+, z') - G(z'^-, z') \\ G'(z'^+, z') - G'(z'^-, z') \end{pmatrix} = \begin{pmatrix} 0 \\ D^{-1}(z') \end{pmatrix} \quad (2.32)$$

where $G'(z, z') \equiv \partial_z G(z, z')$. The general solution of G(z, z') may be written as:

$$G(z, z') = S[e^{-Qz} f^\pm(z') + e^{Qz} g^\pm(z')], \quad (2.33)$$

where $f^\pm(z')$ and $g^\pm(z')$ are square matrices of dimension N to be solved by matching the boundary conditions. The ± sign are for z>z' and z<z', respectively. Due to the fact that the Green's function is originated from the source only, the wave function below the source (z>z') should be obtained using the transfer matrix starting from the substrate and the wave function above the source (z<z') should be obtained by starting from the incident medium. For this reason:

$$g^\pm = R f^+ \text{ and } f^- = \bar{r} g^-,$$

where $\bar{r}$ and R are the reflection matrices obtained from the incident medium and substrate respectively. Subsequently:

$$\begin{pmatrix} G(z'^+, z') - G(z'^-, z') \\ G'(z'^+, z') - G(z'^-, z') \end{pmatrix} = \begin{pmatrix} S & 0 \\ 0 & -SQ \end{pmatrix} \tau \begin{pmatrix} e^{-Qz} & 0 \\ 0 & e^{Qz} \end{pmatrix} \begin{pmatrix} f^+ & -f^- \\ g^+ & -g^- \end{pmatrix} \quad (2.34)$$

$$= \begin{pmatrix} S & 0 \\ 0 & -SQ \end{pmatrix} \tau \begin{pmatrix} e^{-Qz} & 0 \\ 0 & e^{Qz} \end{pmatrix} \begin{pmatrix} 1 & \bar{r} \\ R & 1 \end{pmatrix} \begin{pmatrix} f^+ \\ -g^1 \end{pmatrix}$$

Relating Equation (2.33) to Equation (2.34) yields:

$$\begin{pmatrix} f^+ \\ -g^- \end{pmatrix} = \begin{pmatrix} (1 - \bar{r}R)^{-1} & -\bar{r}(1 - R\bar{r})^{-1} \\ -R(1 - \bar{r}R)^{-1} & (1 - R\bar{r})^{-1} \end{pmatrix} b(z') \quad (2.35)$$

$$= \begin{pmatrix} 1 - \bar{r}uR & -\bar{r}u \\ -uR & u \end{pmatrix} b(z') \quad (2.36)$$

where $u \equiv (1 - R\bar{r})^{-1}$ and:

$$b(z') \equiv \frac{1}{2} \begin{pmatrix} e^{Qz'} \\ -e^{-Qz'} \end{pmatrix} Q^{-1} (DS)^{-1} = \frac{1}{2} \begin{pmatrix} e^{Qz'} \\ -e^{-Qz'} \end{pmatrix} Q^{-1} S^T. \quad (2.37)$$

It can be seen that both $f^+$ and $g^-$ have been uniquely determined. The second form (Equation (2.36)) is required since it guarantees absolute numerical stability for the evaluation of the Green's functions, since explicitly:

$$\begin{pmatrix} f^+ \\ g^- \end{pmatrix} = \frac{1}{2} \begin{pmatrix} e^{Qz'} + \bar{r}u(Re^{Qz'} + e^{-Qz'}) \\ u(Re^{Qz'} + e^{-Qz'}) \end{pmatrix} Q^{-1} S^T. \quad (2.38)$$

Note that all exponentially growing factors $e^{Qz'}$ are accompanied by the factor $R = e^{-Qd} \bar{R} e^{-Qd}$. Thus, in actual calculations $\bar{R}$ and the combined factor $e^{Q(z'-d)}$ are always evaluated to guarantee numerical stability. Hence when both z and z' are inside the same layer, the Green's function is written as:

$$G(z, z') = S \left[ \frac{1}{2} e^{-Q|z-z'|} Q^{-1} S^T + e^{-Qz} \bar{r} g^-(z') + e^{Qz} R f^+(z') \right]. \quad (2.39)$$

Note that the first term is singular, which is different for z>z' and z<z'. The remainder is a regular function, which is the same whether z>z' or z<z'.

For z and z' located in different layers, the transfer-matrix method (similar to that for the wave function as discussed in the previous section) is used to obtain G(z, z') starting from the solution for z at layer l', in which z' is located. For z in a layer l below (z>z'), Equation (2.20) is used repeatedly to obtain the coefficient $f_l^+$ starting from $f_{l'}^-$. Similarly, for z in a layer l above (z<z'), Equation (2.29) is used repeatedly to obtain the coefficient $g_l^-$ starting from $g_{l'}^-$.

The G0 Case

For the G0 case, evaluation of the Green's function is limited to the incident medium (air) that makes up the perturbation domain (i.e., 0<z, z'<d). For the backward transfer, there is no reflection in the incident medium. Thus, $\bar{r}=0$ and S=const. This yields:

$$\begin{pmatrix} f_0^+ \\ -g_0^- \end{pmatrix} = \begin{pmatrix} e^{Qz} \\ -(\bar{R}e^{Qz'} + e^{-Qz'}) \end{pmatrix} \frac{1}{2}Q^{-1}. \tag{2.40}$$

$$G(z, z') = \frac{S^2}{2}[e^{-Q|z-z'|} + e^{-Q(d-z)}\bar{R}e^{-Q(d-z)}]Q^{-1} \tag{2.41}$$

Here $\bar{R}$ is a diagonal matrix with the n-th diagonal entry equal to $r_n$, which corresponds to the reflection coefficient of order n for the zero-th order structure shown in FIG. 3.

The Ga case

For the Ga case, Green's function must be evaluated in the perturbation domain (0<z, z'<d), in which the structure has multiple slices of uniform dielectric medium (labeled with s) with an effective dielectric function $\in^*_s$. $\in^*_s=(\in_s(z)-1)(w_s(z)/p)+1$ is used for TE modes and $1/\in^*_s=(1/\in_s-1)(w_s/p)+1$ is used for TM modes, where $\in_s$ is the dielectric function of the grating material and $w_s$ is the width of grating in slice s at different z. The Green's function is still given by Equation (2.39). However, since all layers are uniform in the x-y plane, all matrices in this equation are diagonal and they can be evaluated much more efficiently.

Numerical Implementation for Two-dimensional Wave Equations

This section describes the use of modeling method to numerically evaluate the two waves equations for two-dimensional structures (Equations (2.4) and (2.9)). This numerical implementation allows the Green's function approach to be used within optical metrology and other systems that require diffraction modeling for two-dimensional structures.

As previously described, the modeling method begins with the creation of an idealized representation for the scatterer (see step 202 of FIG. 2). In the following step (step 204), the perturbation domain (0<z'<d) of the idealized representation is subdivided into a series of M−1 segments. As shown in FIG. 5, the boundaries between the M−1 segments have z' values labeled by $z_0$, $z_1$ and so on through $z_{M-1}$ (with $z_0=0$ and $z_{M-1}=d$). Within each segment, the perturbation V is assumed to be constant. For the simplest case, each segment has the same thickness. In many cases, however, it is desirable to vary the thickness of individual segments to increase accuracy of the numerical implementation. Typically, and as shown in FIG. 5, this is used to provide more segments near boundaries.

The next two steps (206 and 208) are performed separately for TE and TM modes. The TE mode case is described first, followed by the description for TM modes. In step 206 (for TE modes) the Green's function for the G1 case Equation (2.33) is substituted into the Lippmann-Schwinger equation for TE modes Equation (2.4). The resulting integral:

$$\Psi(z)-\Psi_0(z)=\int dz'S[e^{-Qz}f^{\pm}(z')+e^{Qz}g^{\pm}(z')]V(z')\Psi(z') \tag{2.42}$$

is evaluated for each of the segments defined in step 204. To perform this series of evaluations, the wave function within each segment is approximated by a linear interpolation formula. For segment j ($z_{j-1}<z'<z_j$), the interpolation formula is:

$$\Psi(z')=\Psi(z_{j-1})+\Psi'(z_j)(z'-z_{j-1}); j=1, M-1,$$

where $\Psi'(z_j) \equiv [\Psi(z_j)-\Psi(z_{j-1})]/\Delta z$, is the z-derivative of $\Psi(z')$ in segment j and $\Delta z_j = z_j - z_{j-1}$, is mesh size in segment j. In each iteration, the wave function $\Psi$ on the boundary mesh point $z_j$ is updated by carrying out the integral over z' within each segment analytically, thus converting the Lippmann-Schwinger equation into a simple sequence of matrix-vector multiplications.

To increase accuracy, the numerical implementation decomposes the Green's function G(z, z') into two integrals, one proportional to analytic the function $e^{-Qz'}$ and the other proportional to $e^{Qz'}$ [see Equation (2.41)]. These separate terms are contained in each of the G0, G1 and Ga cases. For each segment j, the integrals are:

$$\frac{1}{2}\int_{z_{j-1}}^{z_j} dz' e^{-Qz'} Q^{-1}S^T \Psi(z') = e^{-Qz_{j-1}}[W_j\Psi(z_{j-1}) + W_j^{(-)}\Psi'(z_j)]$$

and:

$$\frac{1}{2}\int_{z_{j-1}}^{z_j} dz' e^{Qz'} Q^{-1}S^T \Psi(z') = e^{Qz_j}[W_j\Psi(z_{j-1}) + W_j^{(+)}\Psi'(z_j)],$$

where:

$$W_j \equiv \frac{1}{2}(1 - e^{-Q\Delta z_j})Q^{-2}S^T,$$

$$W_j^{(-)} \equiv \frac{1}{2}(W_j - \Delta z_j e^{-Q\Delta z_j})Q^{-2}S^T$$

$$W_j^{(+)} \equiv \frac{1}{2}(\Delta z_j - W_j)Q^{-2}S^T.$$

This decomposition is essential for making the Lippmann-Schwinger equations numerically accurate, since it brings down a factor of $Q^{-1}$ that decays like 1/n as the order of the coupled-wave basis increases. Without this extra factor, the TM mode calculation is slow convergent (decaying like 1/n), and a direct numerical evaluation of the Lippmann-Schwinger equation on a finite mesh may be inaccurate.

Evaluating Equation (2.42) over z' in each segment j results in the following system of linear equations:

$$\hat{A}X = X - S(\bar{G}VX + \bar{G}'VX') = X^0, \tag{2.43}$$

where $X^0$, X, and X' are NM-dimensional column vectors with entries $X_n^0(j) = \langle n|\Psi^0(z_j)\rangle$, $X_n(j) = \langle n|\Psi(z_j)\rangle$, and $X'_n(j) = \langle n|\Psi'(z_j)\rangle$. N is the number of coupled waves and M is the number of mesh points in z. V, $\bar{G}$, and $\bar{G}'$ are NM×NM matrices with matrix elements:

$$V_{n,n'}(j, j') = \delta_{j,j'} \langle n|V(z_j)|n'\rangle,$$

$$\overline{G}_{n,n'}(j, j') =$$

$$\begin{cases} \langle n|e^{-Q(z_j-z_f)}W_{j'} + e^{-Q z_j}\bar{r}g^-(j') + e^{Q z_j}Rf^+(j')|n'\rangle, \text{ for } j \geq j' \\ \langle n|e^{-Q(z_j-z_{f-1})}W_{j'} + e^{-Q z_j}\bar{r}g^-(j') + e^{Q z_j}Rf^+(j')|n'\rangle, \text{ for } j < j' \end{cases}$$

$$\overline{G}'_{n,n'}(j, j') =$$

$$\begin{cases} \langle n|e^{-Q(z_j-z_f)}W^{(+)}_{j'} + e^{-Q z_j}\bar{r}g'^-(j') + e^{Q z_j}Rf'^+(j'))|n'\rangle, \text{ for } j \geq j' \\ \langle n|e^{Q(z_j-z_{f-1})}W^{(-)}_{j'} + e^{-Q z_j}\bar{r}g'^-(j') + e^{Q z_j}Rf'^+(j'))|n'\rangle, \text{ for } j < j' \end{cases}$$

where:

$$\begin{pmatrix} f^+(j) \\ g^-(j) \end{pmatrix} = \begin{pmatrix} e^{Q z_j} + \bar{r}u(Re^{Q z_j} + e^{-Q z_{j-1}}) \\ u(Re^{Q z_j} + e^{-Q z_{j-1}}) \end{pmatrix} W_j, \quad (2.44)$$

and:

$$\begin{pmatrix} f'^+(j) \\ g'^-(j) \end{pmatrix} = \begin{pmatrix} e^{Q z_j}W^{(+)}_j + \bar{r}u(Re^{Q z_j}W^{(+)}_j + e^{-Q z_{j-1}}W^{(-)}_j) \\ u(Re^{Q z_j} + e^{-Q_{j-1}}W^{(-)}_j) \end{pmatrix}. \quad (2.45)$$

In step 208, the system of linear equations is solved This can be done using any iterative solver. Typical solvers include the quasi-minimal-residue (QMR), TMRES and Krylov subspace solvers. Other suitable techniques may also be used. In the case where QMR is used, the initial guess of the wave function is taken to be $\Psi^0(z')$ and is calculated via RCWA on the boundary mesh points $z_j$ ($j=1, \ldots M-1$). The matrices S, R, $\bar{r}$, and u are also calculated and stored. These matrices are independent of the perturbation V, allowing them to be computed once and reused. The following numerical procedures are then performed iteratively:

1. Calculate X' from X via the relation:

$$X'(j)=[X(j)-X(j-1)]/\Delta z_j; j=1, \ldots, M-1.$$

2. Perform the matrix-vector operations $VX \equiv Y$ and $VX' \equiv Y'$. This procedure takes $N^2M$ steps. By using symmetric and anti-symmetric combinations of the coupled-wave basis (i.e., define $|n_\pm = |n\rangle + |-n\rangle$), V is block-diagonalized within the symmetrized basis due to the fact that V(x, z) is symmetric in x-space for fixed value of z. In this way, the operation can be speeded up by a factor of two.

3. Perform the matrix-vector multiplications $\overline{G}Y$ and $\overline{G}'Y'$. Here the fact that $\overline{G}$ is semi-separable is utilized allowing the matrix-vector operation to be carried out with just N×M steps. Defining $B=\overline{G}Y$ yields:

$$B(j) = e^{-Q z_j}\sum_{j'=1}^{j} e^{Q z_j}W_{j'}Y(j') + e^{Q z_j}\sum_{j'=j+1}^{M-1} e^{-Q z_{j-1}}W_{j'}Y(j') +$$

$$e^{-Q z_j}\bar{r}\sum_{j'=1}^{M-1}g^-(j')Y(j') + e^{Q z_j}R\sum_{j'=1}^{M-1}f^+(j')Y(j')$$

$$\equiv F_s(j) + G_s(j) + e^{-Q z_j}\bar{r}G_r + e^{Q z_j}RF_r,$$

where the singular parts $F_s(j)$ and $G_s(j)$ are calculated via the recursion relation:

$$F_s(j)=e^{-Q\Delta z_j}F_s(j-1)+W_jY(j)$$

$$G_s(j-1)=e^{-Q\Delta z_j}G_s(j)+W_jY(j)$$

with $F_s(0)=G_s(M-1)=0$, and the regular parts $F_r$ and $G_r$ are calculated via the straightforward summation. Note that in the above expressions, all terms are numerically stable, since all exponentially growing terms like $e^{Q z_j}$ are multiplied by a factor $e^{-Qd}$ extracted from the relation $R=e^{-Qd}\overline{R}e^{-Qd}$. Similarly, $B'=\overline{G}'Y'$ and:

$$B'(j) = F'_s(j) + G'_s(j) + e^{-Q z_j}\bar{r}G'_r + e^{Q z_j}RF'_r,$$

where:

$$F'_s(j) = e^{-Q\Delta z_j}F'_s(j-1) + W^{(+)}_j Y(j)$$

$$G'_s(j-1) = e^{-Q\Delta z_j}G'_s(j) + W^{(-)}_j Y(j)$$

$$F'_r = \sum_r f'^+(j)Y(j),$$

and:

$$G'_r = \sum_j g'^+(j)Y(j).$$

4. Perform the matrix-vector multiplication $S(B-B')$ and calculate $\hat{A}X \equiv X - S(B+B')$. Note that the eigenvalues of $\hat{A}$ are all close to 1 if the magnitude of GV is small compared to 1. This feature makes the QMR method a fast converging one. The iteration procedure involves repeated multiplication of the form $\hat{A}X$.

Once the convergent solutions to X and consequently Y and Y' are obtained, the modeling method completes at step 208 where the following projected Lippmann-Schwinger equation is used to calculate the TE mode reflection coefficients:

$$r=r_0+\int G(0, z')V(z')\Psi(z')dz'=r_0+G^sY+G'^sY' \quad (2.46)$$

where $G^s$, and $G'^s$ are row vectors with entries defined by:

$$G_n^s(j)=\langle 0|S(1+\bar{r})g^-(j)|n\rangle, \text{ and}$$

$$G'^s_n(j)=\langle 0|S(1+\bar{r})g'^-(j)|n\rangle,$$

As mentioned, steps 206 and 208 are repeated separately for TE and TM modes (this separation is logical and the operations may be combined for some implementations). The description for TE modes has just been completed. In step 206 (for TM modes) the Green's function for the G1 case Equation (2.33) is substituted into the Lippmann-Schwinger equation for TM modes Equation (2.9). The resulting integral:

$$\Psi(z) - \Psi^0(z) = \quad (2.47)$$

$$\int dz' \left\{ \begin{array}{l} S[e^{-Qz}f^\pm(z') + e^{Qz}g^\pm(z')]K\tilde{V}(z')K\Psi(z') \\ +\partial_{z'} S[e^{-Qz}f^\pm(z') + e^{Qz}g^\pm(z')]V(z')\partial_{z'}\Psi(z') \end{array} \right\},$$

is evaluated for each of the segments defined in step 204. To perform this series of evaluations, the wave function within each segment is approximated using the same linear interpolation formula used for TE modes. The same method for enhancing the accuracy of the Lippmann-Schwinger equation is also used (i.e., decomposition to form two integrals).

Evaluating equation (2.47) over z' in each segment j results in the following system of linear equations:

$$\hat{A}X \equiv X-S(\overline{G}K\tilde{V}KX+\overline{G}'K\tilde{V}KVX'+d\overline{G}VX)=X^0, \quad (2.48)$$

where K, $\tilde{V}$, and V are the same matrices as introduced in Equation (2.9). $d\overline{G}$ is a NM×NM matrix with elements:

$$dG_{n,n'}(j,j') = \quad (2.49)$$

$$\begin{cases} \langle n|e^{-Q(z_j-z_{j'})}QW_{j'} + e^{-Q z_j}rg_z^-(j') + e^{Q z_j}Rf_z^+(j')|n'\rangle, \text{ for } j \geq j' \\ \langle n|-e^{Q(z_j-z_{j-1})}QW_{j'} + e^{-Q z_j}rg_z^-(j') + e^{Q z_j}Rf_z^+(j')|n'\rangle, \text{ for } j < j', \end{cases}$$

where:

$$\begin{pmatrix} f_z^+(j) \\ g_z^-(j) \end{pmatrix} = \begin{pmatrix} e^{Q z} + \bar{r}u(Re^{Q z_j} - e^{-Q z_{j-1}}) \\ u(Re^{Q z_j} - e^{-Q z_{j-1}}) \end{pmatrix} QW_j.$$

In step 208, the system of linear equations is solved. This can be done using any iterative solver. Typical solvers include the quasi-minimal-residue (QMR), TMRES and Krylov subspace solvers. Other suitable techniques may also be used. In the case where QMR is used, the initial guess of the wave function is taken to be $\Psi^0(z')$ and is calculated via RCWA on the boundary mesh points $z_j$ (j=1, ..., M−1). The matrices S, R, $\bar{r}$, and u are also calculated and stored. These matrices are independent of the perturbation V, allowing them to be computed once and reused. The following numerical procedures are then performed iteratively:

1. Calculate X' from X using the relation:

$$X'(j)=[X(j)-X(j-1)]/\Delta z_j; j=1, \ldots, M-1.$$

2. Perform the matrix-vector operations:

$$K\tilde{V}KX=Y_1, K\tilde{V}KX'=Y_2, \text{ and } VX'=Y'.$$

3. Perform the matrix-vector multiplications:

$$K\tilde{V}KX=Y_1, K\tilde{V}KX'=Y_2, \text{ and } VX'=Y' \; \bar{G}Y_1=B_1, \bar{G}'Y_2=B_2, \text{ and } d\bar{G}Y'=B'.$$

4. Perform the matrix-vector multiplication $S(B_1+B_2+B')$ is performed and calculate $\hat{A}X=X-S(B_1+B_2+B')$. Steps 1 through 4 are repeated until convergent solutions to X and consequently Y, Y', $Y_1$, and $Y_2$ are obtained. Note that the eigenvalues of $\hat{A}$ are all close to 1 if the magnitude of GV is small compared to 1. This feature makes the QMR method a fast converging one. The iteration procedure involves repeated multiplication of the form: $\hat{A}X$.

The numerical implementation is then completed at step 208 where the following the following projected Lippmann-Schwinger equation is used to calculate the TM mode reflection coefficients:

$$r = r_0 + \int G(0, z')V(z')\Psi(z')dz' + \quad (2.50)$$
$$\int \partial_{z'} G(0, z')V(z')\Psi'(z')dz'dz'$$
$$\equiv r_0 + G^s Y_1 + G'^s Y_2 + dG^s Y'$$

where $G^s$, $G'^s$ and $dG^s$ are row vectors with entries defined by:

$$G_n^s(j)=\langle 0|S(1+\bar{r})g^-(j)|n\rangle,$$

$$G'_n^s(j)=\langle 0|S(1+\bar{r})g'^-(j)|n\rangle, \text{ and}$$

$$dG_n^s(j)=\langle 0|S(1+\bar{r})g_z^-(j)|n\rangle.$$

Multi-layer Evaluation

If the perturbation domain contains more than one layer of materials, the transfer-matrix method is used to calculate $\bar{G}Y=B$ (and similarly for B', $B_1$, and $B_2$) due to contributions from z' in different material layers. When z (where the updated wave function is to be evaluated) is in layer l, B is defined as the summation:

$$B = \sum_{l'} B^{(ll')},$$

where $B^{(ll')}$ is the contribution from all z' in layer l'. $B^{(ll')}$ is obtained according to procedure 3 described above. For l>l', each $B^{(ll')}$ is defined as:

$$B^{(ll')}(j)=(e^{-Q_l z_j}+e^{Q_l z_j}R)\bar{T}_{l-1}\bar{T}_l F_r^{(l')},$$

and for l<l', each $B^{(ll')}$ is defined as:

$$B^{(ll')}(j)=(e^{-Q_l z_j}\bar{r}+e^{Q_l z_j})\bar{t}_l\bar{t}_{l-1}G_r^{(l')},$$

where $\bar{T}_l=T_l e^{-Q_l d_l}$ and $\bar{t}_l=e^{-Q_l d_l}t_l$.

Finally, the Born approximation may be used for the G1 case when the zero-th order structure chosen is very close to the physical structure. In this case, the wave function $\Psi$ is replaced by the zero-th order wave function $\Psi^0$ and Equations (2.46) and (2.50) are used to directly evaluate the reflection coefficients.

Equation Section 3 E Field Wave Equation for Three-dimensional Structures

This section describes an E field derivation for a wave equation for three-dimensional structures. The E field wave equation allows the modeling method to be used to predict the diffraction response of three-dimensional structures (i.e., structures that do not exhibit translational symmetry in any one direction). For semi-conductor wafers, this can include patterns of vias and other periodic and non-periodic structures. The E field wave equation may also be used to model scattering for conical incidence.

To describe this derivation, consider a two-dimensional periodic array of three-dimensional gratings. The primitive lattice vectors within this array are labeled $a_1$ and $a_2$. The corresponding primitive reciprocal lattice vectors are denoted $b_1$ and $b_2$ with $b_i \cdot a_j = 2\pi \delta_{ij}$. For this system, the wave function and Green's function may be expanded in terms of the plane wave $e^{i\vec{k}_n \cdot \vec{\delta}}$, where $\vec{k}_n$; n=1, ..., N denotes a series of N reciprocal lattice vectors. The x and y components of $\vec{k}_n$ are conveniently denoted as $k_{xn}$ and $k_{yn}$.

The equations for electric fields are:

$$\nabla \times \nabla \times E = \in k_0^2 E.$$

$$\nabla \cdot \in E = 0,$$

where $k_0 = \omega/c$ is the wave number. The electric field is related to the magnetic field via:

$$H(r) \Box \nabla \times E(r)$$

The dyadic Green's function for the uniform multilayer material is denoted G and satisfies the following equation:

$$\nabla \times \nabla \times G - \in_n(z)k_0^2 G = \nabla \nabla \cdot G - \in_n(z)k_0^2 G = \delta(r'-r) \quad (3.1)$$

where $\in_n$ is the dielectric constant of the host medium and with the boundary conditions that G and $\nabla \times G$ are continuous across z boundaries.

Within the perturbation domain (i.e., 0<z'<d), the periodic nature of the system allows G to be written in terms of coupled-wave basis as:

$$G(r'-r) = \sum_n e^{ik_n \cdot (\rho-\rho')} G_n(z, z') = \sum_n e^{ik_{xn}(x-x')+ik_{yn}(y-y')} G_n(z, z').$$

Substituting this into Equation (3.1) yields:

$$[(ik_n+\hat{z}\partial_z)(ik_n+\hat{z}\partial_z) \cdot G_n + (k_n^2-\partial_z^2)G_n] - \in_n k_0^2 G_n = I\delta(z-z'),$$

where I is a 3×3 identity matrix. Taking the dot product of $(ik_n+\hat{z}\partial_z)$ with the above gives:

$$-\in_n(z)k_0^2(ik_n+\hat{z}\partial_z) \cdot G_n = (ik_n+\hat{z}\partial_z)\delta(z-z'). \quad (3.2)$$

or:

$$(q_n^2 - \partial_z^2)G_n = \left[I + \frac{(ik_n+\hat{z}\partial_z)(ik_n+\hat{z}\partial_z)}{\varepsilon_a k_0^2}\right]\delta(z-z'), \quad (3.3)$$

where $q_n^2 \equiv k_n^2 - \in_n k_0^2$. It is convenient to choose a different coordinate frame (x', y') for each index n, such that $k_n$ is parallel to the x' axis. The following equations are used to make this transformation:

$$\hat{x} = \cos\phi_n \hat{x}' - \sin\phi_n \hat{y}',$$
$$\hat{y} = \sin\phi_n \hat{x}' - \cos\phi_n \hat{y}',$$

where $\phi_n = \tan^{-1}(k_{yn}/k_{xn})$. In this frame, G takes the simplified form:

$$G = \begin{pmatrix} G_{xx} & 0 & G_{xz} \\ 0 & G_{yy} & 0 \\ G_{zx} & 0 & G_{zz} \end{pmatrix}$$

with the boundary conditions that:

$$G_{xx}, G_{xz}, G_{yy}, \frac{\varepsilon_a(z)}{q_n^2}\partial_z G_{xx}, \frac{\varepsilon_n(z)}{q_n^2}\partial_z G_{xz}, \text{ and } \partial_z G_{yy}$$

are all continuous across z boundaries.

The y'y' component of G is simply:

$$G_{yy} = \frac{1}{2q_n}\left[e^{-q_n|z-z'|} + e^{q_n z'} R_n f_n(z) + e^{-q_n z'} \vec{r}_n g_n(z)\right],$$

where $f_n(z)$ and $g_n(z)$ are given by (in column vector form):

$$\begin{pmatrix} f \\ g \end{pmatrix} = \begin{pmatrix} e^{Qz} + \bar{r}u(\bar{R}e^{Qz} + e^{-Qz}) \\ u(\bar{R}e^{Qz} + e^{-Qz}) \end{pmatrix}, \quad (3.4)$$

where $u = (1-R\bar{r})^{-1}$. Q denotes a square matrix with diagonal entries $q_n$. R and $\tilde{r}$ are the forward and backward transfer matrices which can be obtained by the transfer matrix method.

$G_{xx}$ and $G_{xz}$ are given by:

$$G_{xx} = \frac{-q_n}{2\varepsilon_n k_0^2}\left[e^{-q_n|z-z'|} + e^{q_n z'} \tilde{R}_n \tilde{f}_n(z) + e^{-q_n z'} \tilde{r}_n \tilde{g}_n(z)\right],$$

$$G_{xz} = \frac{ik_n}{2\varepsilon_n k_0^2}\left[sgn(z'-z)e^{-q_n|z-z'|} - e^{q_n z'} \tilde{R}_n \tilde{f}_n(z) + e^{-q_n z'} \tilde{r}_n \tilde{g}_n(z)\right],$$

where $\tilde{f}_n$ and $\tilde{g}_n$ takes the same as $f_n$ and $g_n$ except the related $\tilde{R}_n$ and $\tilde{r}_n$ are obtained with different boundary conditions.

Equations (3.2) and (3.3) are used to relate the remaining two components to $G_{xx}$ and $G_{xz}$ via:

$$G_{zx} = \frac{-ik_n}{q_n^2}\partial_z G_{xx}$$

$$G_{zz} = \frac{1}{q_n^2}[-ik_n\partial_z G_{xz} + \delta(z-z')].$$

resulting in:

$$G_{zx} = \frac{ik_n}{2\varepsilon_a k_0^2}\left[sgn(z'-z)e^{-q_n|z-z'|} - e^{q_n z'} \tilde{R}_n \tilde{f}_n(z) + e^{-q_n z'} \tilde{r}_n \tilde{g}_n(z)\right],$$

$$G_{zz} = \frac{k_n^2}{2q_n \varepsilon_a k_0^2}\left[e^{-q_n|z-z'|} + e^{q_n z'} \tilde{R}_n \tilde{f}_n(z) + e^{-q_n z'} \tilde{r}_n \tilde{g}_n(z)\right] - \frac{1}{\varepsilon_a k_0^2}\delta(z-z'), \text{ where:}$$

$$\begin{pmatrix} \bar{f} \\ \bar{g} \end{pmatrix} \equiv \begin{pmatrix} Q^{-1}\frac{d}{dz}\tilde{f} \\ Q^{-1}\frac{d}{dz}\tilde{g} \end{pmatrix} = \begin{pmatrix} e^{Qz} + \tilde{r}\tilde{u}(\tilde{R}e^{Qz} + e^{-Qz}) \\ \tilde{u}(\tilde{R}e^{Qz} + e^{-Qz}) \end{pmatrix}. \quad (3.5)$$

Note that G(r, r') is symmetric, which implies $G(k_n; z, z') = G^T(-k_n; z', z)$. Here: $G(k_n; z, z') = G_n(z, z')$. Rotating back to the original coordinates yields:

$$G_n = \begin{pmatrix} G_{11} & G_{12} & G_{13} \\ G_{21} & G_{22} & G_{23} \\ G_{31} & G_{32} & G_{33} \end{pmatrix} =$$

$$\begin{pmatrix} \cos^2\phi_n G_{xx} + \sin^2\phi_n G_{yy} & \cos\phi_n\sin\phi_n(G_{xx}-G_{yy}) & \cos\phi_n G_{xz} \\ \cos\phi_n\sin\phi_n(G_{xx}-G_{yy}) & \sin^2\phi_n G_{xx} + \cos^2\phi_n G_{yy} & \sin\phi_n G_{xz} \\ \cos\phi_n G_{zx} & \sin\phi_n G_{zx} & G_{zx} \end{pmatrix}.$$

It can be shown that the following Lippmann-Schwinger equation holds:

$$\Psi(z) - \Psi^0(z) = \int dz' G(z, z')V(z')\Psi(z'), \quad (3.6)$$

where $V \equiv (\in(z) - \in_n)k_0^2$. Note that $\in(z)$ is anisotropic in the laminated film in the grating region:

$$\varepsilon = \begin{pmatrix} P^{-1} & 0 & 0 \\ 0 & \varepsilon & 0 \\ 0 & 0 & \varepsilon \end{pmatrix},$$

where P as a matrix in the coupled-wave basis is the inverse of the $\in$ matrix. For 3D gratings, it is assumed that the dielectric tensor takes the form:

$$\varepsilon = \begin{pmatrix} P^{-1} & 0 & 0 \\ 0 & P^{-1} & 0 \\ 0 & 0 & \varepsilon \end{pmatrix}.$$

The three-component Lippmann-Schwinger equation can be reduced to a two-component Lippmann-Schwinger equation by utilizing the transverse condition $\nabla \cdot \in E = 0$ to eliminate one component ($E_x$). The resulting equation is:

$$\tilde{E}_x = P^{-1}E_x = K_x^{-1}[i\partial_z(\in E_z) - K_y(\in E_y)].$$

Substituting this into the Lippmann-Schwinger equation (for the y and z components) yields:

$$E_y(z) - E_y^0(z) = \int dz' [G_{21}\tilde{V}\tilde{E}_x + G_{22}VE_y + G_{23}VE_z], \quad (3.7)$$

$$E_z(z) - E_z^0(z) = \int dz' [G_{31}\tilde{V}\tilde{E}_x + G_{32}VE_y + G_{33}VE_z], \quad (3.8)$$

where $\tilde{V}$ is defined as:

$$\tilde{V} \equiv (1 - P\varepsilon_n)k_0^2.$$

Note that both V and $\tilde{V}$ can be factored out as the product of a complex number and a real toeplitz matrix, and the product $\varepsilon E_i = VE_i + \varepsilon_n E_i$, i=x, y can be calculated quickly once $VE_i$ are obtained. In the special case with $K_y = 0$, $E_z$ is proportional to $K_x \varepsilon^{-1} H_y$, and the above Lippmann-Schwinger equations reduce to two decoupled integral equations, one for the TE mode ($E_y$) and the other for the TM mode ($H_y$). The resulting decoupled Lippmann-Schwinger equations are identical to those derived previously for the special limit (G0 approach):

$$E_y(z) - E_y^0(z) = \int dz' G_{22}(z, z') V E_y, \quad (3.9)$$

$$H_y - \tilde{E}_z^0(z) = \int dz' [\partial_{z'} \overline{G}(z, z') \tilde{V} \partial_{z'} H_y + \overline{G}(z, z') K_x V \varepsilon^{-1} K_n H_y], \quad (3.10)$$

where:

$$\overline{G}(z, z') = \frac{1}{2q_n k_0^2} [e^{-q_n|z-z'|} - e^{q_n z'} \tilde{R}_n \overline{f}_n(z) + e^{-q_n z'} \tilde{r}_n \overline{g}_n(z)].$$

Numerical Evaluation for the E Field Wave Equation for Three-Dimensional Structures This section describes the use of modeling method to numerically evaluate the wave equation for three-dimensional structures (Equation (3.6)). This numerical implementation allows the Green's function approach to be used within optical metrology and other systems that require diffraction modeling for three dimensional structures.

Figure 6:
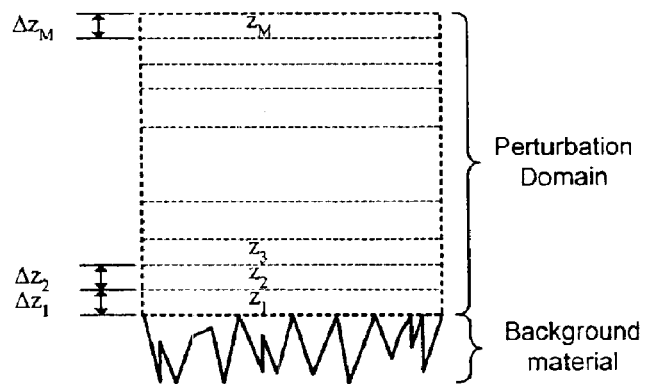
FIG. 6 is a cross sectional representation of the perturbation domain of the G0 structure after an alternate subdivision.

As previously described, the modeling method begins with the creation of an idealized representation for the scatterer (see step 202 of FIG. 2). In the following step (step 204), the perturbation domain (0<z'<d) of the idealized representation is subdivided into a series of M segments. As shown in FIG. 6, the width of each $j^{th}$ segment is labeled $\Delta z_j$. The corresponding midpoint of each $j^{th}$ segment is labeled $z_j$. Within each segment, the perturbation function V is assumed to be constant. For the simplest case, each segment has the same thickness. In many cases, however, it is desirable to vary the thickness of individual segments to increase accuracy of the numerical implementation. Typically, and as shown in FIG. 6, this is used to provide more segments near boundaries.

In step 206, Equation (3.6) is evaluated for each of the segments defined in step 204. To perform this series of evaluations, the wave function within each segment is approximated by its value at the midpoint $z_j$. In each iteration, the wave function $\Psi$ on the boundary mesh point $z_j$ is updated by carrying out the integral over z' within each segment analytically, converting the Lippmann-Schwinger wave equation into a sequence of matrix-vector multiplications.

Note that in all cases the green's function G(z, z') contains terms that are proportional to the analytic functions $e^{-Qz'}$ or $e^{Qz'}$. The Lippmann-Schwinger equation contains the following integrals, which are carried out analytically within each segment. For segment j, the integrals are:

$$\int_{z_j^-}^{z_j^+} dz' e^{-Qz'} \Psi(z') = e^{-Q(z_j-)} W_j \Psi(z_j)$$

and $$\int_{z_j^-}^{z_j^+} dz' e^{Qz'} \Psi(z') = e^{Q(z_j+)} W_j \Psi(z_j)$$

where $z_j^\pm \equiv z_j \pm \Delta z_j/2$ and $$W_j \equiv (1 - e^{-Q\Delta z_j}) Q^{-1}.$$

The above procedure is essential for making the Lippmann-Schwinger equations accurate, since it brings down a factor of $Q^{-1}$ which decays like 1/n as the order of the coupled-wave basis increases. Without this extra factor, the calculation is slow convergent (decaying like 1/N), and a direct numerical evaluation of the Lippmann-Schwinger equation on a finite mesh may be inaccurate. Performing an average of the resulting function of Equation (3.6) over z within each segment j further improves accuracy. This brings down another factor of $Q^{-1}$. If z and z' fall into the same segment j, the result is:

$$\int_{z_j^-}^{z_j^+} dz \int_{z_j^-}^{z_j^+} dz' e^{-Q|z-z'|} = W_j^0. \quad (3.11)$$

where:

$$W_j^0 = 2[\Delta z - (1 - e^{-Q\Delta z}) Q^{-1}] Q^{-1}.$$

and:

$$\int_{z_j^-}^{z_j^+} dz \int_{z_j^-}^{z_j^+} dz' sgn(z'-z) e^{-Q|z-z'|} = 0.$$

The result of the double integration is the following system of linear equations:

$$\hat{A}X \equiv X - \tilde{G}VX + (VX)_z \varepsilon_n k_0^2 = X^0, \quad (3.12)$$

Within Equation (3.12) $X^0$ and $X$ are 3NM-dimensional column vectors where N is the number of coupled waves in each direction of x and y, and M (as previously discussed) is the number of subdivisions of the perturbation domain. The elements of $X^0$ and $X$ are defined as:

$$X_n^0(j) = \langle n|\Psi^0(z_j)\rangle \text{ and}$$

$$X_n(j) = \langle n|\Psi(z_j)\rangle.$$

V and $\overline{G}$ are 3NM×3NM matrices with matrix elements given by:

$$V_{n,n'}(j, j') = I\delta_{j,j'} n|V(z_j)|n',$$

$$\overline{G}(j, j') = \begin{cases} S^0 W_j^0 \delta_{j,j'} + W_j [Se^{-Q|z_j^- - z_{j'}^+|} \theta(j > j') \\ + S' e^{-Q|z_j^+ - z_{j'}^-|} \theta(j < j') + RF(j) e^{Qz_{j'}^+} \\ + \tilde{r}G(j) e^{-Qz_j^-}] W_{j'} \end{cases}$$

where $R(\tilde{r})$ is a 3N×3N matrix with diagonal elements being $\tilde{R}_n(\tilde{r}_n)$ for the x'x' and zz components and $R_n(\tilde{r}_n)$ for the y'y' component. $S^0$, S, S', f(j) and g(j) are 3N×3N matrices with the $n^{th}$ diagonal block given by:

$$S_n = \begin{pmatrix} \frac{-q_n^2}{\varepsilon_a k_0^2} & 0 & \frac{-ik_n q_n}{\varepsilon_a k_0^2} \\ 0 & 1 & 0 \\ \frac{-ik_n q_n}{\varepsilon_a k_0^2} & 0 & \frac{k_n^2}{q_n \varepsilon_a k_0^2} \end{pmatrix} / 2q_n \Delta z$$

$S^0$ is obtained from S by eliminating the off-diagonal terms.

$$S'_n = \begin{pmatrix} \frac{-q_n^2}{\varepsilon_a k_0^2} & 0 & \frac{ik_n q_n}{\varepsilon_a k_0^2} \\ 0 & 1 & 0 \\ \frac{ik_n q_n}{\varepsilon_a k_0^2} & 0 & \frac{k_n^2}{\varepsilon_a k_0^2} \end{pmatrix} / 2q_n \Delta z$$

$$F_n(j) = \begin{pmatrix} \frac{-q_n^2}{\varepsilon_a k_0^2} \overline{f}_n(j) & 0 & \frac{ik_n q_n}{\varepsilon_a k_0^2} \overline{f}_n(j) \\ 0 & f_n(j) & 0 \\ \frac{ik_n q_n}{\varepsilon_a k_0^2} \overline{f}_n(j) & 0 & \frac{-k_n^2}{\varepsilon_a k_0^2} \overline{f}_n(j) \end{pmatrix} / 2q_n \Delta z$$

$$G_n(j) = \begin{pmatrix} \frac{-q_n^2}{\varepsilon_a k_0^2} \overline{g}_n(j) & 0 & \frac{ik_n q_n}{\varepsilon_a k_0^2} \overline{g}_n(j) \\ 0 & g_n(j) & 0 \\ \frac{ik_n q_n}{\varepsilon_a k_0^2} \overline{g}_n(j) & 0 & \frac{k_n^2}{\varepsilon_a k_0^2} \overline{g}_n(j) \end{pmatrix} / 2q_n \Delta z$$

$$\begin{pmatrix} f(j) \\ g(j) \end{pmatrix} = \begin{pmatrix} e^{Qz_j^+} + \overline{r}u(Re^{Qz_j^+} - e^{-Qz_j^-}) \\ u(Re^{Qz_j^+} + e^{-Qz_j^-}) \end{pmatrix}.$$

$\tilde{f}_n$ and $\tilde{g}_n$ takes the same as $f_n$ and $g_n$ except $R_n$ and $\bar{r}_n$ are replaced by $\tilde{R}_n$ and $\tilde{r}_n$.

$$\begin{pmatrix} \overline{f}(j) \\ \overline{g}(j) \end{pmatrix} = \begin{pmatrix} e^{Qz} + \overline{ru}(\overline{R}e^{Qz_j^+} - e^{-Qz_j^-}) \\ \overline{u}(\overline{R}e^{Qz_j^+} - e^{-Qz_j^-}) \end{pmatrix}.$$

In step 208, the system of linear equations is solved. This can be done using any iterative solver. Typical solvers include the quasi-minimal-residue (QMR), TMRES and Krylov subspace solvers. Other suitable techniques may also be used.

In the case where QMR is used, the initial guess of the wave function $\Psi(z')$ is taken to be $\Psi^0(z')$ which is evaluated on the mesh points $z_j$ ($j=1, \ldots, M$). The following numerical procedures are then performed:

1. Perform the matrix-vector operations VX≡Y. In general, this calculation can take $N^2M$ steps, making it a potential computational bottleneck for the numerical implementation. To improve efficiency, the vector X is transformed into real space before performing the operation VX. The product VX is then transformed back into k-space. The CPU time scales like MNlogN for such a procedure, because the transformation can be done independently for the x and y directions. This scheme is feasible only if the dielectric tensor in the grating region is assumed to be isotropic (a reasonable approximation for low contrast medium).

2. Perform the matrix-vector multiplication $\overline{G}Y$. Here the fact that $\overline{G}$ is semi-separable is utilized allowing the matrix-vector operations to be carried out in N×M steps, Letting $B=\overline{G}Y$, yields:

$$B(j) =$$

$$S^0 W_j^0 Y(j) + W_j \left[ S e^{-Qz_j} \sum_{j'=1}^{j-1} e^{Qz_{j'}^+} W_{j'} Y(j') + S' e^{Qz_j^+} \sum_{j'=j+1}^{M} e^{-Qz_{j'}} W_{j'} Y(j') + \right.$$

-continued $$\left. Rf(j) \sum_{j'=1}^{M} e^{Qz_{j'}^+} W_{j'} Y(j') + \overline{r}g(j) \sum_{j'=1}^{M} e^{-Qz_{j'}} W_{j'} Y(j') \right] \equiv$$

$$S^0 W_j^0 Y(j) + W_j [SF_s(j) + S'G_s(j) + Rf(j)F_r + \overline{r}g(j)G_r],$$

where the singular parts $F_s(j)$ and $G_s(j)$ are calculated via the recursion relations:

$$F_s(j) = e^{-Q\Delta z_{j-1}} F_s(j-1) + W_{j-1} Y(j-1)$$

$$G_s(j-1) = e^{-Q\Delta z_j} G_s(j) + W_j Y(j)$$

with $F_s(1) = G_s(M) = 0$, and the regular parts $F_r$ and $G_r$ are calculated via the straightforward summation. Note that in the above expressions, all terms are numerically stable, since all exponentially growing terms like $e^{Qz_j}$ are multiplied by a factor $e^{-Qd}$ extracted out from the relation $R = e^{-Qd} \overline{R} e^{-Qd}$.

3. Calculate $\hat{A}X \equiv X - B + (VX)_z / \varepsilon_a k_0^2$.

Note that the eigen-values of $\hat{A}$ are all close to 1 if the magnitude of GV is small compared to 1. This feature makes the QMR method a fast converging one. The iteration procedure involves repeated multiplication of the form $\hat{A}X$.

Two-component Equation Section 4H Field Wave Equation for Three-dimensional Structures This section describes a derivation for an H field wave equation for three-dimensional structures. The H field wave equation allows the modeling method to be used to predict the diffraction response of three-dimensional structures (i.e., structures that do not exhibit translational symmetry in any one direction). For semi-conductor wafers, this can include patterns of vias and other periodic and non-periodic structures. The H field wave equation may also be used to model scattering for conical incidence.

The derivation for TM modes begins with the equation:

$$\nabla \times \varepsilon^{-1} \nabla \times \vec{H} = k_0^2 \vec{H}$$

where $k_0$ is the wave number and is equal to $\omega/c$. In coupled wave terms, this can be rewritten as:

$$\vec{H}(x, y, z) = \vec{H}(z) e^{i(K_x x + K_y y)},$$

where H(z) is a column vector of dimension $N^2$, and $K_x$, $K_y$ denote $N^2 \times N^2$ square matrices with diagonal entries equal to $(k_{0x} + 2n\pi/p)$ and $(k_{0y} + 2m\pi/p)$; n, m=1, . . . , N. $k_z = -i\partial_z$ remains a scalar. The requirement (from the Maxwell equations) that $\nabla \cdot \vec{H} = 0$ gives:

$$k_z H_z = -(K_x H_x + K_y H_y)$$

leading to the following equations for magnetic fields:

$$-\hat{x} \cdot \{\vec{k} \times \varepsilon^{-1} [-(K_x H_z - k_z H_x) \hat{y} - (K_x H_y - K_y H_x) \hat{z}]\}$$

$$= -k_z \varepsilon^{-1} (K_x H_z - k_z H_x) - K_y \varepsilon^{-1} (K_x H_y - K_y H_x)$$

$$= k_z \varepsilon^{-1} k_z^{-1} (K_x K_y H_y + K_x K_x H_x) + k_z \varepsilon^{-1} k_z H_x - K_y \varepsilon^{-1} (K_x H_y - K_y H_x)$$

$$= k_0^2 H_x$$

$$-\hat{y} \cdot \{\vec{k} \times \varepsilon^{-1} [(K_y H_z - k_z H_y) \hat{x} + (K_x H_y - K_y H_x) \hat{z}]\}$$

$$= -k_z \varepsilon^{-1} (K_y H_z - k_z H_y) + K_x \varepsilon^{-1} (K_x H_y - K_y H_x)$$

$$= k_z \varepsilon^{-1} k_z^{-1} (K_y K_x H_x - K_x K_y H_y) + k_z \varepsilon^{-1} k_z H_y) + K_x \varepsilon^{-1} (K_x H_y - K_y H_x)$$

$$= k_0^2 H_y$$

or:

$$\begin{pmatrix} k_0^2 - k_z \varepsilon^{-1} k_z^{-1} K_x^2 - K_y \varepsilon^{-1} K_y & K_y \varepsilon^{-1} K_x - k_z \varepsilon^{-1} k_z^{-1} K_x K_y \\ K_x \varepsilon^{-1} K_y - k_z \varepsilon^{-1} k_z^{-1} K_y K_x & k_0^2 - k_z \varepsilon^{-1} k_z^{-1} K_y^2 - K_x \varepsilon^{-1} K_x \end{pmatrix} \begin{pmatrix} H_x \\ H_y \end{pmatrix} = \quad (4.1)$$

$$k_z \varepsilon^{-1} k_z \begin{pmatrix} H_x \\ H_y \end{pmatrix}$$

The relationship between magnetic fields and electric fields can be obtained as:

$$-k_0 \in E_x = k_z H_y - K_y H_z = k_z H_y + k_z^{-1} K_y (K_x H_x + K_y H_y),$$

$$k_0 \in E_y = k_z H_x - k_x H_z = k_z H_x + k_z^{-1} K_x (K_x H_x + K_y H_y).$$

or:

$$-k_0 k_z \in E_x = k_z^2 H_y + K_y K_x H_x + K_y^2 H_y,$$

$$k_0 k_z \in E_y = k_z^2 H_x + K_x^2 H_x + K_x K_y H_y.$$

Assuming that:

$$\Psi = \begin{pmatrix} H_x \\ H_y \end{pmatrix} \text{ and } \Psi' = \begin{pmatrix} E_y \\ -E_x \end{pmatrix},$$

produces the following differential equations:

$$[\partial_z P(z) \partial_z - L(z)] \Psi = 0, \quad (4.2)$$

$$\Psi' = P(z) \partial_z \Psi, \quad (4.3)$$

where:

$$L(z) = -k_0^2 I + \begin{pmatrix} K_y \varepsilon^{-1} K_y & -K_y \varepsilon^{-1} K_x \\ -K_x \varepsilon^{-1} K_y & +K_x \varepsilon^{-1} K_x \end{pmatrix}, \quad (4.4)$$

where I is the identity matrix, and:

$$P(z) = \begin{pmatrix} \varepsilon^{-1} & 0 \\ 0 & \varepsilon^{-1} \end{pmatrix} \left[ I + \begin{pmatrix} K_x^2 & K_x K_y \\ K_y K_x & K_y^2 \end{pmatrix} k_z^{-2} \right] \equiv \begin{pmatrix} \varepsilon^{-1} & 0 \\ 0 & \varepsilon^{-1} \end{pmatrix} (I + \eta k_z^{-2}).$$

The wave function $\Psi$ satisfies the boundary conditions that $\Psi(z)$ and $P(z)\partial_z \Psi(z)$ are continuous across z boundaries.

The derivation for TE modes begins with the equation:

$$\nabla \times \nabla \times \vec{E} = \in k_0^2 \vec{E}.$$

where $k_0$ is the wave number and is equal to $\omega/c$. In coupled wave terms, this can be rewritten as:

$$\vec{E}(x, y, z) = \vec{E}(z) e^{i(K_x x + K_y y)},$$

where E(z) is a column vector of dimension $N^2$, and $K_x$, $K_y$ denote $N^2 \times N^2$ square matrices with diagonal entries equal to $(k_{0x} + 2n\pi/p)$ and $(k_{0y} + 2m\pi/p)$; n, m=1, . . . , N. $k_z = -i\partial_z$ remains a scalar. The requirement (from the Maxwell equations) that $\nabla \cdot \vec{E} = 0$ gives:

$$k_z \in E_z = -(K_x \in E_x + K_y \in E_y)$$

leading to the following equations for electric fields:

$$-\hat{x} \cdot \{ \vec{k} \times [-(K_x E_z - k_z E_x) \hat{y} - (K_x E_y - K_y E_x) \hat{z}] \}$$

$$\vert -k_z (K_x E_z - k_z E_x) - K_y (K_x E_y - K_y E_x)$$

$$= k_z \in^{-1} k_z^{-1} (K_x K_y \in E_y + K_x K_x \in E_x) + k_z k_z E_x - K_y (K_x E_y - K_y E_x)$$

$$= \in k_0^2 E_x$$

$$-\hat{y} \cdot \{ \vec{k} \times [(K_y E_z - k_z E_y) \hat{x} + (K_x E_y - K_y E_x) \hat{z}] \}$$

$$\vert -k_z (K_y E_z - k_z E_y) + K_x (K_x E_y - K_y E_x)$$

$$= K_y k_z \in^{-1} k_z^{-1} (K_x \in E_x + K_y \in E_y) + k_z k_z E_y) + K_x (K_x E_y - K_y E_x)$$

$$= \in k_0^2 E_y$$

or:

$$\begin{pmatrix} \in k_0^2 - k_z \varepsilon^{-1} k_z^{-1} K_x^2 \varepsilon - K_y^2 & K_y \varepsilon^{-1} K_x \varepsilon - k_z \varepsilon^{-1} k_z^{-1} K_x K_y \varepsilon \\ K_x K_y - k_z \varepsilon^{-1} k_z^{-1} K_y K_x \varepsilon & \in k_0^2 - k_z \varepsilon^{-1} k_z^{-1} K_y^2 \varepsilon - K_x K_x \end{pmatrix} \begin{pmatrix} E_x \\ E_y \end{pmatrix} = \quad (4.5)$$

$$k_z^2 \begin{pmatrix} E_x \\ E_y \end{pmatrix}$$

The relationship between magnetic fields and electric fields can be obtained as:

$$-k_0 \in E_x = k_z E_y - K_y E_z = k_z E_y + k_z^{-1} K_y (K_x E_x + K_y E_y),$$

$$k_0 \in E_y = k_z E_x - k_x E_z = k_z E_x + k_z^{-1} K_x (K_x E_x + K_y E_y).$$

or:

$$-k_0 k_z \in E_x = k_z^2 E_y + K_y K_x E_x + K_y^2 E_y,$$

$$k_0 k_z \in E_x = k_z^2 E_x + K_x^2 E_x + K_x K_y E_y.$$

Assuming that:

$$\Psi = \begin{pmatrix} E_x \\ E_y \end{pmatrix} \text{ and } \Psi' = \begin{pmatrix} E_y \\ -E_x \end{pmatrix},$$

produces the following differential equations:

$$[\partial_z P(z) \partial_z - L(z)] \Psi = 0, \quad (4.6)$$

$$\Psi' = P(z) \partial_z \Psi, \quad (4.7)$$

where:

$$L(z) = -k_0^2 I + \begin{pmatrix} K_y \varepsilon^{-1} K_y & -K_y \varepsilon^{-1} K_x \\ -K_x \varepsilon^{-1} K_y & +K_x \varepsilon^{-1} K_x \end{pmatrix}, \quad (4.8)$$

where I is the identity matrix, and:

$$P(z) = \varepsilon^{-1} \left[ I + \begin{pmatrix} K_x^2 & K_x K_y \\ K_y K_x & K_y^2 \end{pmatrix} k_z^{-2} \right] \equiv \varepsilon^{-1} (I + \eta k_z^{-2}).$$

The wave function $\Psi$ satisfies the boundary conditions that $\Psi(z)$ and $P(z)\partial_z \Psi(z)$ are continuous across z boundaries.

The Green's function for the G0 structure is defined by:

$$G \begin{pmatrix} G_x & G_{xy} \\ G_{yx} & G_y \end{pmatrix},$$

which satisfies:

$$[\partial_z P_0(z) \partial_z - L_0(z)] G(z - z') = \delta(z - z') I, \quad (4.9)$$

where:

$$P_0(z) = \in_0(z)^{-1} (I + \eta k_z^{-2})$$

$$L_0 = -k_0^2 I + \begin{pmatrix} K_y \epsilon_0^{-1} K_y & -K_y \epsilon_0^{-1} K_x \\ -K_x \epsilon_0^{-1} K_y & K_x \epsilon_0^{-1} K_x \end{pmatrix}.$$

Note that for uniform multilayer systems, $\epsilon_0^{-1}$ commutes with $K_x$ and $K_y$ with the result that: $[\partial_z P_0(z) \partial_z - L_0(z)] = [\partial_z \epsilon_0(z)^{-1} \partial_z + \epsilon_0(z)^{-1}(K_x^2 + K_y^2) - k_0^2]I$. The Green's function must satisfy the same boundary conditions for $\Psi$. Namely that $G(z, z')$ and $P_0(z)\partial_z G(z, z')$ are continuous across z boundaries.

For coupled wave within the perturbation domain (for $0 < z < d$):

$$G = \frac{1}{p^2} \sum_{m,n} e^{ik_{xn}(x-x') + ik_{ym}(y-y')} \frac{1}{q_{nm}} \left[ e^{-q_{nm}|z-z'|} + e^{q_{nm}^2} R_{nm} e^{q_{nm}z'} \right],$$

where $q_{nm} = \sqrt{k_{xn}^2 + k_{ym}^2 - \epsilon_0 k_0^2}$. In the coupled-wave basis, G can be expressed as a $2N^2$-dimensional square matrix in the form:

$$G(z, z') = \frac{1}{2} Q^{-1} \left[ e^{-Q|z-z'|} + e^{Qz} R e^{Qz'} \right], \quad (4.10)$$

where Q is a diagonal matrix with entries $q_{nm}$.

The reflection matrix R is obtained by the transfer matrix method. It is convenient to choose a different coordinate frame (x', y') for each index nm, such that $P_0(z)$ is diagonal. This produces:

$$H_{x'} = \cos \phi_{nm} H_x + \sin \phi_{nm} H_y,$$

$$H_{y'} = -\sin \phi_{nm} H_x + \cos \phi_{nm} H_y,$$

where $\phi_{nm} = \tan^{-1}(k_{ym}/k_{xn})$. The reflection amplitudes for $H_{x'}$ and $H_{y'}$ fields are simply $R_{nm}^{x'} = -R_{nm}^s$ and $R_{nm}^{y'} = R_{nm}^p$. Here s and p denote the TE and TM modes for a conically incident wave with wave vector $(k_{xn}, k_{ym}, k_{0z})$. Rotating back to the original coordinates yields:

$$R_{nm} = \begin{pmatrix} \cos^2 \phi_{nm} R_{nm}^x + \sin^2 \phi_{nm} R_{nm}^p & \cos \phi_{nm} \sin \phi_{nm}(R_{nm}^x - R_{nm}^p) \\ \cos \phi_{nm} \sin \phi_{nm}(R_{nm}^x - R_{nm}^p) & \sin^2 \phi_{nm} R_{nm}^x + \cos^2 \phi_{nm} R_{nm}^p \end{pmatrix}.$$

Note that $P_0(z)$, $L_0$ and $G$ are all symmetric matrices. Taking the transpose of Equation (4.5) yields:

$$[\partial_z P_0(z') \partial_z G(z'-z) - G(z'-z) L_0(z')] = \delta(z-z') I, \quad (4.11)$$

Multiplying the above equation by $(\Psi - \Psi_0)$ and Equation (4.1) by $G(z, z')$ and integrating each result over z' produces the following equations:

$$\int dz' [-\partial_z P_0(z') \partial_z G(z', z) + G(z', z) L_0(z)] [\Psi(z') - \Psi_0(z')] = \Psi(z) - \Psi_0(z)$$

and $$\int dz' G(z, z') [\partial_z P(z') \partial_z - L(z)] \Psi(z') = 0.$$

Subtracting these equations and performing an integration by parts leads to the Lippmann-Schwinger equation:

$$\Psi(z) - \Psi_0(z) = \int dz [G(z, z') V(z') \Psi(z') + (\partial_z G(z, z')) \Delta(z') (\partial_{z'} \Psi(z'))], \quad (4.12)$$

$$V \equiv L(z) - L_0(z) = \begin{pmatrix} K_y D(z) K_y & -K_y D(z) K_x \\ -K_x D(z) K_y & K_x D(z) K_x \end{pmatrix}, \quad (4.13)$$

$D(z) = \epsilon^{-1}(z) - \epsilon_0^{-1}(z)$, and $\Delta(z) = P(z) - P_0(z) = D(z)(I + \eta k_z^{-2})$. Note that the boundary terms generated by the integration by parts vanish due to the fact both $\Psi(z) P_0(z) \partial_z G(z, z')$ and $G(z, z') P(z) \partial_z \Psi(z)$ are continuous across a z boundary. Here $k_z = -i\partial_z$ and $k_z^{-1} = -i\int_z^\infty dz$. $k_z^{-1}$ is defined in this way so that $k_z k_z^{-1} = 1$. This avoids an arbitrary constant term, since $\Psi(z) = 0$ as $z \to \infty$. $V(z)$ and $D(z)$ are non-zero only in the perturbation domain $0 < z < d$. However, the last term in Equation (4.7) involves an integration operator $k_z^{-1}$, which means that $\Psi(z)$ must be solved for $0 < z < \infty$. The problem is simplified by defining an integration constant $C \equiv \int_d^\infty \Psi(z)$ so that Equation (4.7) now reads:

$$\Psi(z) - \Psi_0(z) = \quad (4.14)$$

$$\int_0^d dz' \left\{ \begin{array}{l} G(z, z') V(z') \Psi(z') \\ + [\partial_{z'} G(z, z')] D(z') \left[ \partial_{z'} \Psi(z') + \eta \left( C + \int_{z'}^d \psi(z'') dz'' \right) \right] \end{array} \right\}$$

Integrating Equation (4.7) over z in the domain $d < z < \infty$ produces the following auxiliary equation for C:

$$C - C^0 = \quad (4.15)$$

$$\int_0^d dz' \left\{ \begin{array}{l} G(z') V(z') \Psi(z') \\ + [\partial_{z'} G(z')] D(z') \left[ \partial_{z'} \Psi(z') + \eta \left( C + \int_{z'}^d \psi(z'') dz'' \right) \right] \end{array} \right\}$$

where $C^0 \equiv \int_d^\infty dz \Psi(z)$ and $G(z') \equiv \int_d^\infty dz G(z, z')$, which can be carried out analytically. The above two coupled equations can now be solved via numerical method. For the incident waves $$\Psi_0 = \begin{pmatrix} 0 \\ H_x^0 \end{pmatrix}$$

is used for TM modes and $$\Psi_0 = \begin{pmatrix} H_y^0 \\ 0 \end{pmatrix}$$

is used for TE modes. In the perturbation domain $0 < z < d$ this produces:

$$H_y^0 \Box e^{ik_0 x + ik_0 z} + r_p e^{ik_0 x - ik_0 z}.$$

$$H_x^0 \Box e^{ik_0 x + ik_0 z} + r_s e^{ik_0 x - ik_0 z}.$$

$$E_y^0 \Box e^{ik_0 x + ik_0 z} + r_s e^{ik_0 x - ik_0 z}.$$

Note that $H_x^0$ $E_y^0$ are related by $H_x^0 = k_z E_y^0 / k_0$ with $r_s = -r_x$. The final result for the reflection amplitude obtained for the $H_x$ field must also change sign to get the reflection amplitude for TE modes.

For a layer l in the region $z > d > z'$, $\Psi_0$ and G take the form:

$$\Psi_0(z) = [e^{-Qz_l} + e^{Qz_l} R_l] C_l,$$

$$G(z, z') = [e^{-Qz_l} + e^{Qz_l} R_l] f_l(z'),$$

where $z_l = z - t_l$ is the z coordinate relative to the position of the interface between layers L and l-1. $R_l$ is the reflection matrix at layer l and $C_l$ and $f_l$ are obtained via the recursion relation:

$$C_{l+1} = T_l e^{-Q_l d_l} C_l$$

$$f_{l+1}(z') = T_l e^{-Q_l d_l} f_l(z')$$

starting from l=1 (for 0<z'<d) with $C_l$ and:

$$f_1(z') = \frac{1}{2} e^{Q_1 z'} Q_1^{-1}.$$

$C_l$ is a $2N^2$ column vector with the only non-zero entry at n=m=0 for the $H_x$ or $H_y$ component. $T_l$ is the transfer matrix defined above. This produces:

$$C^0 = \sum_{l=2}^{L} C_l[1 - e^{-Q_l d_l} + R_l(e^{Q_l d_l} - 1)]Q_l^{-1} + C_{L+1} Q_{L+1}^{-1}$$

and:

$$G(z') = \sum_{l=2}^{L} f_l(z')[1 - e^{-Q_l d_l} + R_l(e^{Q_l d_l} - 1)]Q_l^{-1} + f_{L+1}(z')Q_{L+1}^{-1}$$

$$\equiv \frac{1}{2} F e^{Q_1(z'-d)} Q_1^{-1},$$

where $d_l$ is the thickness of layer l; l=1, ..., L and $d_l$=d. L+1 is the label for the substrate material. Denote the results for $F(C^0)$ obtained above for $H_{x'}$ and $H_{y'}$ in the (x', y') frame for nm(00)-component as $F_{nm}^{x}(C_x^0)$ and $F_{nm}^{y}(C_y^0)$. Rotating back to the original frame yields:

$$F_{nm} = \begin{pmatrix} \cos^2\phi_{nm} F_{nm}^x + \sin^2\phi_{nm} F_{nm}^y & \cos\phi_{nm}\sin\phi_{nm}(F_{nm}^x - F_{nm}^y) \\ \cos\phi_{nm}\sin\phi_{nm}(F_{nm}^x - F_{nm}^y) & \sin^2\phi_{nm} F_{nm}^x + \cos^2\phi_{nm} F_{nm}^y \end{pmatrix},$$

and:

$$C^0 \begin{pmatrix} \cos\phi_{00} C_x^0 & -\sin\phi_{00} C_y^0 \\ \sin\phi_{00} C_x^0 & \cos\phi_{00} C_y^0 \end{pmatrix}.$$

Numerical Evaluation for the H-field Wave Equation for Three-dimensional Structures This section describes the use of modeling method to numerically evaluate the wave equation for three-dimensional structures (Equation (4.12)). This numerical implementation allows the Green's function approach to be used within optical metrology and other systems that require diffraction modeling for three dimensional structures.

As previously described, the modeling method begins with the creation of an idealized representation for the scatterer (see step 202 of FIG. 2). In the following step (step 204), the perturbation domain (0<z'<d) of the idealized representation is subdivided into a series of M−1 segments. As shown in FIG. 5, the boundaries between the M−1 segments have z' values labeled by $z_0$, $z_1$ and soon through $z_{M-1}$ (with $z_0$=0 and $z_{M-1}$=d). Within each segment, the perturbation V is assumed to be constant. For the simplest case, each segment has the same thickness. In many cases, however, it is desirable to vary the thickness of individual segments to increase accuracy of the numerical implementation. Typically, and as shown in FIG. 5, this is used to provide more segments near boundaries.

In step 206, the Green's function for the G0 case Equation (4.10) is substituted into the Lippmann-Schwinger equation [Equation (4.12)] and the resulting integral is evaluated for each of the M−1 segments. To perform this series of evaluations, the wave function within each segment is approximated by a linear interpolation formula. For segment j ($z_{j-1}$<z'<$z_j$), the interpolation formula is:

$$\Psi(z') = \Psi(z_{j-1}) + \Psi'(z_j)(z' - z_{j-1}); \quad j=1, M-1,$$

where $\Psi'(z_j) \equiv [\Psi(z_j) - \Psi(z_{j-1})]/\Delta z_j$ is the z-derivative of $\Psi(z')$ in segment j. $\Delta z_j = z_j - z_{j-1}$ is mesh size in segment j. In each iteration, the wave function $\Psi$ on the boundary mesh point $z_j$ is updated by carrying out the integral over z' within each segment analytically, thus converting the Lippmann-Schwinger equations into a simple sequence of matrix-vector multiplications.

To increase accuracy, the numerical implementation decomposes the Green's function G(z, z') into two integrals, one proportional to analytic the function $e^{-Qz'}$ and the other proportional to $e^{Qz'}$ [see Equation (4.10)]. These separate terms are contained in each of the G0, G1 and Ga cases. For each segment j, the integrals are:

$$\frac{1}{2} \int_{z_{j-1}}^{z_j} dz' e^{-Qz'} Q^{-1} S^T \Psi(z') = e^{-Qz_{j-1}}[W_j \Psi(z_{j-1}) + W_j^{(-)} \Psi'(z_j)]$$

and:

$$\frac{1}{2} \int_{z_{j-1}}^{z_j} dz' e^{Qz'} Q^{-1} S^T \Psi(z') = e^{Qz_j}[W_j \Psi(z_{j-1}) + W_j^{(+)} \Psi'(z_j)]_n$$

where:

$$W_j \equiv \frac{1}{2}(1 - e^{-Q\Delta z_j}) Q^{-2} S^T,$$

$$W_j^{(-)} \equiv \frac{1}{2}((1 - e^{-Q\Delta z_j}) Q^{-1} - \Delta z_j e^{-Q\Delta z_j}) Q^{-2} S^T$$

$$W_j^{(+)} \equiv \frac{1}{2}(\Delta z_j - (1 - e^{-Q\Delta z_j}) Q^{-1}) Q^{-2} S^T.$$

This decomposition is essential for making the Lippmann-Schwinger equations numerically accurate, since it brings down a factor of $Q^{-1}$ that decays like 1/n as the order of the coupled-wave basis increases. Without this extra factor, the TM mode calculation is slow convergent (decaying like 1/N), and a direct numerical evaluation of the Lippmann-Schwinger equation on a finite mesh may be inaccurate.

Substituting Equation (4.10) into the L-S equation [Equation (4.12)] and carrying out the integral over z' in each segment j results in the following system of linear equations:

$$\hat{A}X \equiv X - [\bar{G}VX + \bar{G}'VX' + d\bar{G}D(X' + \eta(C + \tilde{X}))] = X^0, \quad (4.16)$$

with:

$$\hat{A}C \equiv C - [\bar{G}VX + \bar{G}'VX' + d\bar{G}D(X' + \eta(C + \tilde{X}))] = C^0$$

where $X^0$, X, X' and $\tilde{X}$ are $N^2M$-dimensional column vectors with entries:

$$X_{nm}^0(j) = <nm|\Psi^0(z_j)>,$$

$$X_{nm}(j) = <nm|\Psi(z_j)>,$$

$$X'_{nm}(j) = <nm|\Psi'(z_j)>, \text{ and}$$

$$\tilde{X}_{nm}(j) = nm|\int_{z_j}^{d} dz \Psi(z_j).$$

N is the number of coupled waves in each direction of x and y, and M is the number of mesh points in z. V $\bar{G}$, $\bar{G}'$, and d $\bar{G}$ are $2N^2M \times 2N^2M$ matrices with matrix elements:

$$V_{nm,n'm'}(j, j') = \delta_{j,j'} <nm|V(z_j)|n'm'>,$$

$$\tilde{G}_{nm,n'm'}(j,j') = \delta_{nm,n'm'} \begin{cases} (e^{-Q(z_j-z_f)} + e^{Qz_j}R_{nm}e^{Qz_f}]W_j, & \text{for } j \geq j' \\ (e^{Q(z_j-z_{f-1})} + e^{Qz_j}R_{nm}e^{Qz_f})W_j, & \text{for } j < j' \end{cases}$$

$$\tilde{G}'_{nm,n'm'}(j,j') = \delta_{nm,n'm'} \begin{cases} (e^{-Q(z_j-z_f)} + e^{Qz_j}R_{nm}e^{Qz_f}]W_j^{(+)}, & \text{for } j \geq j' \\ (e^{Q(z_j-z_{f-1})} + e^{Qz_j}R_{nm}e^{Qz_f})W_j^{(-)}, & \text{for } j < j' \end{cases}$$

$$d\tilde{G}_{nm,n'm'}(j,j') = \delta_{nm,n'm'} \begin{cases} (e^{-Q(z_j-z_f)} + e^{Qz_j}R_{nm}e^{Qz_f}]QW_j, & \text{for } j \geq j' \\ (-e^{Q(z_j-z_{f-1})} + e^{Qz_j}R_{nm}e^{Qz_f})QW_j, & \text{for } j < j' \end{cases}.$$

where $\tilde{R}=R(1+\bar{r}uR)$, $\overline{G}$, $\overline{G}'$, and $d\overline{G}$ are $2N^2 \times 2N^2 M$ matrices with matrix elements:

$$\overline{G}_{nm,n'm'}(j') = \delta_{nm,n'm'} F_{nm} e^{Q(z_j-d)} W_{j'},$$

$$\overline{G}'_{nm,n'm'}(j') = \delta_{nm,n'm'} F_{nm} e^{Q(z_j-d)} W_{j'}^{(+)},$$

$$d\overline{G}_{nm,n'm'}(j') = \delta_{nm,n'm'} F_{nm} e^{Q(z_j-d)} Q W_{j'}.$$

In step 208, the system of linear equations is solved. This can be done using any iterative solver. Typical solvers include the quasi-minimal-residue (QMR), TMRES and Krylov subspace solvers. Other suitable techniques may also he used. In the case where QMR is used, the initial guess of the wave function is taken to be $\Psi^0(z')$ and is calculated via RCWA on the boundary mesh points $z_j$ ($j=1, \ldots, M-1$). The following numerical procedures are then performed iteratively:

1. Calculate X' and $\tilde{X}$ from X via the relations:

$X'(j)=[X(j)-X(j-1)]/\Delta z_j, j=1,\ldots,M-1.$ and:

$\tilde{X}(j)=\Sigma_{j'=j}^{M-2}[X(j')+X(j'+1)]\Delta z_{j+1}, j=0,\ldots,M-2.$ 2. Perform the matrix-vector operations $VX \equiv Y$, $VX' \equiv Y'$ and $D[X'+\eta(C+\tilde{X})] \equiv Y_z$. In general, this calculation can take $N^4M$ making it a potential computation bottleneck for the numerical implementation. To improve efficiency, the vector X is transformed into real space before performing the operation VX. The VX operation then becomes a simple combination of derivatives and multiplications. The product VX is then transformed back into k-space. CPU time scales on the order of $2MN^3$ for such a procedure. This is because the transformation can be done independently for the x and y directions.

3. Perform the matrix-vector multiplications $\overline{G}Y$, $\overline{G}'Y'$, and $d\overline{G}'Y_z$. Here the fact that $\overline{G}$ is semi-separable is utilized allowing the matrix-vector operation to be carried out with just $N^2 \times M$ steps. Letting $B=\overline{G}Y$ results in:

$$B(j) = e^{-Qz_j} \sum_{j'=1}^{j} e^{Qz_{j'}} W_{j'} Y(j') + e^{Qz_j} \sum_{j'=j+1}^{M-1} e^{-Qz_{f-1}} W_{j'} Y(j') +$$

$$e^{Qz_j} R \sum_{j'=1}^{M-1} e^{Qz_f} W_{j'} Y(j') \equiv F_s(j) + G_s(j) + e^{Qz_j} RF_r,$$

where the singular parts $F_s(j)$ and $G_s(j)$ are calculated via the recursion relation:

$F_s(j) = e^{-Q\Delta z_j} F_s(j-1) + W_j Y(j)$ $G_s(j-1) = e^{-Q\Delta z_j} G_s(j) + W_j Y(j).$ with $F_s(0)=G_s(M-1)=0$, and the regular parts $F_r$ and $G_r$ are calculated via the straightforward summation. Note that in the above expressions, all terms are numerically stable, since all exponentially growing terms like $e^{Qz_j}$ are multiplied by a factor $e^{-Qd'}$ extracted out from the relation $R=e^{-Qd}\overline{R}e^{-Qd}$. Similarly, $B'=\overline{G}'Y'$ and:

$B'(j)=F'_s(j)+G'_s(j)+e^{Qz_j}RF'_r,$ where:

$F'_s(j)=e^{-Q\Delta z_j}F'_s(j-1)+W_j^{(+)}Y(j)$ $G'_s(j-1)=e^{-Q\Delta z_j}G'_s(j)+W_j^{(-)}Y(j)$ and $$F'_r = \sum_j e^{Qz_j} W_j^{(+)} Y(j).$$

Similarly, $B_z=d\overline{G}Y_z$.

4. Calculate $\hat{A}X \equiv X-(B+B'+B_z)$ and $\hat{A}C \equiv C-(\overline{G}Y+\overline{G}'Y'+d\overline{G}Y_z)$.

Note that the eigen-values of $\hat{A}$ are all close to 1 if the magnitude of GV is small compared to 1. This feature makes the QMR method a fast converging one. The iteration procedure involves repeated multiplication of the form $\hat{A}X$.

Once the convergent solutions to X and C and consequently Y, Y', and $Y_z$ are obtained, the modeling method completes at step 208 where the following projected Lippmann-Schwinger equation is used to calculate the reflection coefficients:

$$r = r_0 + \int G(0,z')V(z')\Psi(z')dz' + \int \partial_{z'} G(0,z')\Delta(z')\Psi'(z')dz' \equiv \quad (4.17)$$

$$r_0 + G^s Y + G'^s Y' + dG' Y_z$$

$G^s, G'^s$ and $dG^s$ are row vectors with entries defined by:

$G_{nm}^s(j) = <0|[e^{-Qz_j}+Re^{Qz_j}]W_j|nm>,$ $G'_{nm}^s(j) = <0|[e^{-Qz_j}+Re^{Qz_j}]W_j^{(-)}|nm>,$ $dG_{nm}^s(j) = <0|[e^{-Qz_j}+Re^{Qz_j}]QW_j|nm>.$

Representative Application

Figure 7:
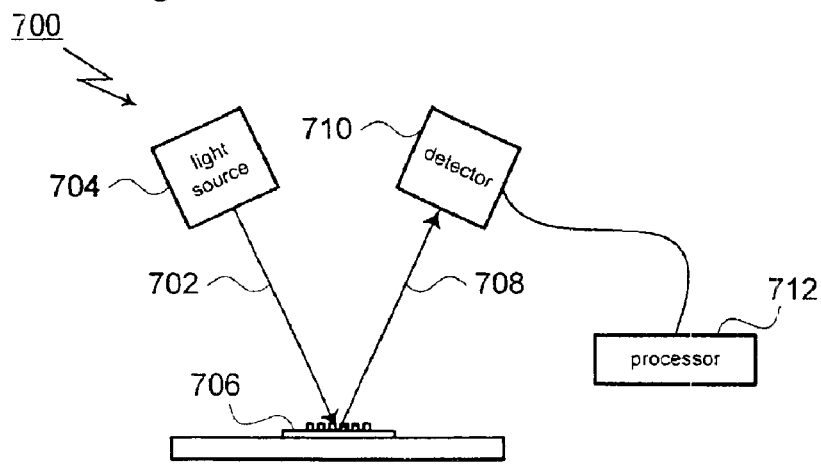
FIG. 7 is block diagram of an optical metrology shown as a representative application for the modeling method of the present invention.

The modeling method and the associated derivations can be used to predict the optical scattering produced by a wide range of structures. FIG. 7 shows the elements of a scatterometer which may be used to generate empirical measurements for optical scattering. As shown in FIG. 7, the scatterometer 700 generates a probe beam 702 using an illumination source 704. Depending on the type of scatterometer 700, the illumination source 704 may be mono or polychromatic. The probe beam 702 is directed at a subject 706 to be analyzed. The subject 706 is generally of the type shown in FIG. 1. The reflected probe beam 708 is received by a detector 710. Once received, changes in reflectivity or polarization state of the probe beam are measured as a function of angle of incidence or wavelength (or both) and forwarded to processor 712.

To analyze the changes measured by detector 710, a hypothetical structure is postulated for the subject 706. Method 100 is then used to calculate one or more predicted reflection coefficients for the hypothetical structure. The hypothetical structure is then changed, and Method 100 repeated, until the predicted reflection coefficients match the results empirically observed by detector 710 (within some predetermined goodness of fit). At this point the hypothetical structure is assumed to closely match the actual structure of subject 706. In practice, modeling method 100 has been found to impart a high degree of efficiency to this process, allowing the analysis of results in real or near real-time. Modeling method 100 may also be used to pre-compute results for a hypothetical structure or for a series of variations to a hypothetical structure. Typically, the pre-computing of results is used as part of a library-based approach where the measurements recorded by detector 710 are compared (at least initially) to predicted reflection coefficients that have been computed and stored ahead of time. This sort of approach may be mixed with the real-time analysis where modeling method 100 is used to refine an analysis initially performed using the library-based approach.

What is claimed is:

1. A method for modeling the diffraction resulting from the interaction of a probe beam with a subject, the method comprising:

defining a zero-th order structure for the subject, the zero-th order structure including a perturbation domain to represent a scatterer within the subject, the zero-th order structure also including a background material to representing the material within the subject that is below the scatterer;

solving a K space Lippmann-Schwinger equation including terms for a wave function for the zero-th order structure, a Green's function for the zero-th order structure and a perturbation function for the perturbation domain.

2. A method as recited in claim 1 wherein the zero-th order structure in the perturbation domain has an optical response equivalent to a foreground material, where the foreground material is the substance that overlays the scatterer.

3. A method as recited in claim 1 wherein the perturbation domain consists of a limited number of square slabs arranged in a repeating pattern.

4. A method as recited in claim 1 wherein the perturbation domain consists of a uniform medium that has an optical response that is computed as a function of the dielectric function for the scatterer and the dielectric function of the substance that overlays the scatterer.

5. A method as recited in claim 1 that further comprises the steps of:

generating a system of linear equations by evaluating the wave equation for the zero-th order structure at a series of points within the perturbation domain; and solving the system of linear equations to obtain one or more reflection coefficient for the zero-th order structure.

6. A method as recited in claim 5 further comprising the step of using an iterative technique to solve the system of linear equations.

7. A method as recited in claim 5 that further comprises the steps of:

subdividing the perturbation domain into a series of segments; and evaluating the wave equation for the zero-th order structure within each segment.

8. A method as recited in claim 7 that further comprises the steps of:

decomposing the Green's function for the zero-th order structure into a first integral proportional to $e^{-Qz'}$ and a second integral proportional to $e^{Qz'}$; and analytically evaluating the first and second integral for each segment.

9. A method as recited in claim 7 that further comprises the step of approximating the wave function for the zero-th order structure within each segment.

10. A method for modeling the diffraction resulting from the interaction of a probe beam with a subject, the method comprising the step of evaluating a k-space volume integral of a Green's function without boundary terms.

11. A method as recited in claim 10 that further comprises the step of: defining a zeroth order structure for the subject, the zero-th order structure including a perturbation domain to represent a scatterer within the subject and a background material to represent the material within the subject that is below the scatterer.

12. A method as recited in claim 11 wherein the zero-th order structure in the perturbation domain has an optical response equivalent to a foreground material, where the foreground material is the substance that overlays the scatterer.

13. A method as recited in claim 11 wherein the perturbation domain consists of a limited number of square slabs arranged in a repeating pattern.

14. A method as recited in claim 11 wherein the perturbation domain consists of a uniform medium that has an optical response that is computed as a function of the dielectric function for the scatterer and the dielectric function of the substance that overlays the scatterer.

15. A method as recited in claim 11 that further comprises the step of solving a K space Lippmann-Schwinger equation including terms for a wave function for the zero-th order structure, a Green's function for the zero-th order structure and a perturbation function for the perturbation domain.

16. A method as recited in claim 15 that further comprises the steps of:

generating a system of linear equations by evaluating the wave equation for the zero-th order structure at a series of points within the perturbation domain; and solving the system of linear equations to obtain a reflection coefficient for the zero-th order structure.

17. A method as recited in claim 16 further comprising the step of using an iterative technique to solve the system of linear equations.

18. A method as recited in claim 15 that further comprises the steps of:

subdividing the perturbation domain into a series of segments; and evaluating the wave equation for the zero-th order structure within each segment.

19. A method as recited in claim 18 that further comprises the steps of:

decomposing the Green's function for the zero-th order structure into a first integral proportional to $e^{-Qz'}$ and a second integral proportional to $e^{Qz'}$; and analytically evaluating the first and second integral for each segment.

20. A method as recited in claim 18 that further comprises the step of approximating the wave function for the zero-th order structure within each segment.

21. A method for modeling the diffraction resulting from the interaction of a probe beam with a subject, the method comprising evaluating a volume integral scattering equation where the wave vector has been reduced to two components using an integration operator to k inverse to represent $k_z$.

22. A method for modeling the diffraction resulting from the interaction of a probe beam with a subject, the method comprising evaluating a volume integral of a Green's function with no boundary terms for the H field.

23. A method for modeling the diffraction resulting from the interaction of a probe beam with a subject, the method comprising:

defining a perturbation domain to represent a scatterer within the subject where the perturbation domain consists of a limited number of square slabs arranged in a repeating pattern; and evaluating a volume integral of a Green's function within the perturbation domain.

24. A method for modeling the diffraction resulting from the interaction of a probe beam with a subject, the method comprising:

defining a zero-th order structure for the subject, the zero-th order structure including a perturbation domain to represent a scatterer within the subject, the zero-th order structure also including a background material to representing the material within the subject that is below the scatterer; and using a separable property of the Green's function to solve a Lippmann-Schwinger wave equation for the zero-th order structure.

25. A method of optically inspecting and evaluating a subject comprising the steps of:

(a) illuminating the subject with a probe light beam;

(b) measuring the light reflected from the subject to generate at least one empirical reflection coefficient;

(c) defining a hypothetical structure corresponding to the subject;

(d) calculating a predicted reflection coefficient for the hypothetical structure by evaluating a k-space volume integral of a Green's function without boundary terms; and (e) repeating steps (c) and (d) until the difference between the predicted reflection coefficient and the empirical reflection coefficient is minimized.

26. A method as recited in claim 25 that further comprises the step of:

defining a zero-th order structure for the subject, the zero-th order structure including a perturbation domain to represent a scatterer within the subject and a background material to represent the material within the subject that is below the scatterer.

27. A method as recited in claim 26 wherein the zero-th order structure in the perturbation domain has an optical response equivalent to a foreground material, where the foreground material is the substance that overlays the scatterer.

28. A method as recited in claim 26 wherein the perturbation domain consists of a limited number of square slabs arranged in a repeating pattern.

29. A method as recited in claim 26 wherein the perturbation domain consists of a uniform medium that has an optical response that is computed as a function of the dielectric function for the scatterer and the dielectric function of the substance that overlays the scatterer.

30. A method as recited in claim 26 that further comprises the step of solving a K space Lippmann-Schwinger equation including terms for a wave function for the zero-th order structure, a Green's function for the zero-th order structure and a perturbation function for the perturbation domain.

31. A method as recited in claim 30 that further comprises the steps of:

generating a system of linear equations by evaluating the wave equation for the zero-th order structure at a series of points within the perturbation domain; and solving the system of linear equations to obtain a reflection coefficient for the zero-th order structure.

32. A method as recited in claim 31 further comprising the step of using an iterative technique to solve the system of linear equations.

33. A method as recited in claim 30 that further comprises the steps of:

subdividing the perturbation domain into a series of segments; and evaluating the wave equation for the zero-th order structure within each segment.

34. A method as recited in claim 33 that further comprises the steps of:

decomposing the Green's function for the zero-th order structure into a first integral proportional to $e^{-Qz'}$ and a second integral proportional to $e^{Qz'}$; and analytically evaluating the first and second integral for each segment.

35. A method as recited in claim 33 that further comprises the step of approximating the wave function for the zero-th order structure within each segment.

* * * * *